(12) United States Patent
Chmiel et al.

(10) Patent No.: US 10,779,731 B2
(45) Date of Patent: Sep. 22, 2020

(54) METHOD AND SYSTEM FOR MONITORING AND MANAGING PATIENT CARE

(75) Inventors: Alan Chmiel, Avon Lake, OH (US);
Heather Gornik, Cleveland, OH (US);
John R. Bartholomew, Cleveland, OH (US); Carlos Grodsinsky, Hinkley, OH (US); Jonathan Schaffer, Moreland Hills, OH (US)

(73) Assignees: THE CLEVELAND CLINIC FOUNDATION, Cleveland, OH (US); ZTECH, INC., Middleburg Heights, OH (US)

( * ) Notice: Subject to any disclaimer, the term of this patent is extended or adjusted under 35 U.S.C. 154(b) by 2155 days.

(21) Appl. No.: 12/857,118

(22) Filed: Aug. 16, 2010

(65) Prior Publication Data
US 2011/0040572 A1    Feb. 17, 2011

Related U.S. Application Data

(60) Provisional application No. 61/234,420, filed on Aug. 17, 2009.

(51) Int. Cl.
*G16H 40/60*    (2018.01)
*A61B 5/00*    (2006.01)
(Continued)

(52) U.S. Cl.
CPC .......... *A61B 5/0002* (2013.01); *A61B 5/4833* (2013.01); *A61B 5/7465* (2013.01);
(Continued)

(58) Field of Classification Search
USPC .......................................... 705/2
See application file for complete search history.

(56) References Cited

U.S. PATENT DOCUMENTS 5,307,263 A    4/1994 Brown
5,390,238 A    2/1995 Kirk et al.
(Continued)

OTHER PUBLICATIONS

Deals roundup: ZIN Technologies and Cleveland Clinic form spin-off company. Medical Device Daily. Sep. 22, 2008.*
(Continued)

*Primary Examiner* — John A Pauls
(74) *Attorney, Agent, or Firm* — Tarolli, Sundheim, Covell & Tummino LLP

(57) ABSTRACT

A patient management system includes a patient unit that obtains results data from a patient device and provides for two-way communication between the patient unit and a remote database. The patient unit can communicate with the remote database to obtain encounter instruction data for a given encounter as well as to send response data for the given encounter. A back office system can also access the database to retrieve the patient data for one or more patient users. The back office system can further add or modify encounter instruction data for use during a next encounter at the patient unit. The back office system can also set a dosage for the patient that can be stored in the remote database and retrieved by the patient unit as part of the given encounter. The back office system may also employ a rules engine that can be programmed according to an established protocol and can automatically generate encounter instructions and dosage information for one or more patient.

29 Claims, 8 Drawing Sheets

(51) Int. Cl.
| | |
|---|---|
| *G06Q 50/22* | (2018.01) |
| *G06F 19/00* | (2018.01) |
| *G06Q 10/10* | (2012.01) |
| *G16H 10/20* | (2018.01) |
| *G16H 40/20* | (2018.01) |
| *A61B 5/145* | (2006.01) |
| *A61B 5/0205* | (2006.01) |

(52) U.S. Cl.
CPC ......... *G06F 19/3418* (2013.01); *G06Q 10/10* (2013.01); *G06Q 50/22* (2013.01); *G16H 10/20* (2018.01); *G16H 40/20* (2018.01); *A61B 5/0205* (2013.01); *A61B 5/145* (2013.01)

(56) References Cited

U.S. PATENT DOCUMENTS

| | | | |
|---|---|---|---|
| 5,471,382 A | 11/1995 | Tallman et al. | |
| 5,601,435 A | 2/1997 | Quy | |
| 5,721,676 A * | 2/1998 | Bolden | A61M 1/387 422/72 |
| 5,832,448 A | 11/1998 | Brown | |
| 5,889,855 A | 5/1999 | Brown | |
| 5,997,476 A * | 12/1999 | Brown | 600/300 |
| 6,046,051 A | 4/2000 | Jina | |
| 6,050,940 A | 4/2000 | Braun | |
| 6,060,323 A | 5/2000 | Jina | |
| 6,066,504 A | 5/2000 | Jina | |
| 6,161,095 A | 12/2000 | Brown | |
| 6,168,563 B1 * | 1/2001 | Brown | 600/301 |
| 6,246,992 B1 | 6/2001 | Brown | |
| 6,334,778 B1 * | 1/2002 | Brown | 434/258 |
| 6,381,577 B1 | 4/2002 | Brown | |
| 6,473,805 B2 | 10/2002 | Lewis | |
| 6,578,002 B1 | 6/2003 | Derzay et al. | |
| 6,588,670 B2 | 7/2003 | Bukowski | |
| 6,640,214 B1 | 10/2003 | Nambudiri et al. | |
| 6,673,622 B1 | 1/2004 | Jina | |
| 6,731,311 B2 | 5/2004 | Bufe et al. | |
| 6,755,783 B2 | 6/2004 | Cosentino et al. | |
| 6,758,810 B2 | 7/2004 | Lebel et al. | |
| 6,871,211 B2 | 3/2005 | Labounty et al. | |
| 6,968,375 B1 * | 11/2005 | Brown | 709/224 |
| 6,980,958 B1 | 12/2005 | Surwit et al. | |
| 7,050,984 B1 | 5/2006 | Kerpelman et al. | |
| 7,056,289 B2 | 6/2006 | Kasper et al. | |
| 7,223,236 B2 * | 5/2007 | Brown | 600/300 |
| 7,228,315 B2 | 6/2007 | Finitzo et al. | |
| 7,252,636 B2 | 8/2007 | Brown | |
| 7,273,454 B2 | 9/2007 | Raymond et al. | |
| 7,301,451 B2 | 11/2007 | Hastings | |
| 7,320,000 B2 | 1/2008 | Brown | |
| 7,396,330 B2 | 7/2008 | Banet et al. | |
| 7,408,439 B2 | 8/2008 | Wang et al. | |
| 7,411,510 B1 | 8/2008 | Nixon | |
| 7,413,438 B2 | 8/2008 | Bisogno | |
| 7,428,494 B2 * | 9/2008 | Hasan et al. | 705/3 |
| 7,440,904 B2 * | 10/2008 | Hasan et al. | 705/3 |
| 7,475,020 B2 * | 1/2009 | Hasan et al. | 705/3 |
| 7,509,264 B2 * | 3/2009 | Hasan et al. | 705/3 |
| 7,533,030 B2 * | 5/2009 | Hasan et al. | 705/2 |
| 7,664,660 B2 * | 2/2010 | Korpman et al. | 705/2 |
| 7,685,003 B2 * | 3/2010 | Hasan et al. | 705/2 |
| 7,693,730 B2 * | 4/2010 | Hasan et al. | 705/2 |
| 7,707,047 B2 * | 4/2010 | Hasan et al. | 705/3 |
| 7,720,691 B2 * | 5/2010 | Hasan et al. | 705/2 |
| 7,831,446 B2 * | 11/2010 | Korpman et al. | 705/2 |
| 8,000,984 B2 * | 8/2011 | Hasan et al. | 705/3 |
| 8,073,710 B2 * | 12/2011 | Hasan et al. | 705/2 |
| 8,131,563 B2 * | 3/2012 | Hasan et al. | 705/2 |
| 2004/0176978 A1 * | 9/2004 | Simon | B60R 25/2018 705/35 |
| 2005/0115561 A1 | 6/2005 | Stahmann et al. | |
| 2005/0191716 A1 | 9/2005 | Surwit et al. | |
| 2007/0073266 A1 | 3/2007 | Chmiel et al. | |
| 2007/0179734 A1 | 8/2007 | Chmiel et al. | |
| 2008/0059228 A1 * | 3/2008 | Bossi et al. | 705/2 |
| 2008/0097170 A1 * | 4/2008 | Brown | 600/301 |
| 2008/0160500 A1 | 7/2008 | Fuller et al. | |
| 2008/0194924 A1 * | 8/2008 | Valk et al. | 600/301 |
| 2008/0243544 A1 * | 10/2008 | Cafer | G06Q 10/10 705/2 |

OTHER PUBLICATIONS

"Professionla User Guide InRatio™ 2 PT Monitoring System"; Inverness Medical; Sep. 25, 2009.*

Publication, "Understanding the Anticoagulant Medication (Coumadin®)", Cleveland Clinic, Copyright 1995-2007, pp. 1-23.

* cited by examiner

| Due Date | Patient | PT | INR | Status | Doctor | Last Updated | Unsched |
|---|---|---|---|---|---|---|---|
| 06/10/2009 | Marsh, Stan | | | Questionaire Complete | Stuart, Richard Lee | 04/17/2009 | |
| 06/10/2009 | Cartman, Eric | | | Questionaire Complete | Geisel, Theodore | 04/17/2009 | |
| 06/10/2009 | McCormick, Kenny | | | Questionaire Complete | Geisel, Theodore | 04/17/2009 | |
| 06/10/2009 | Slydell, Bob | | | Questionaire Complete | Octavius, Otto | 06/09/2009 | ✉ |
| 06/10/2009 | Brofslovski, Kyle | | | Questionaire Complete | Werkmurdigliebe, Doktor | 04/17/2009 | |
| 06/10/2009 | Stotch, Leopold | 54.1 | 5.2 | Form Complete | Geisel, Theodore | 06/22/2009 | |
| 06/10/2009 | Porter, Bob | | | Data Reviewed | Werkmurdigliebe, Doktor | 07/01/2009 | |
| 06/10/2009 | Brofslovski, Ike | 55 | 3.6 | Form Complete | Jeckyll, Henry | 06/22/2009 | |
| 06/10/2009 | Brofslovski, Ike | 4.2 | 4.2 | Form Complete | Jeckyll, Henry | 06/22/2009 | ✉ |
| 06/10/2009 | Brofslovski, Ike | 58.1 | 5.1 | Questionaire Complete | Jeckyll, Henry | 06/22/2009 | ✉ |
| 06/10/2009 | Brofslovski, Ike | | | Questionaire Complete | Jeckyll, Henry | 06/22/2009 | ✉ |

FIG. 9

Encounter Information

PATIENT INFORMATION — 162

- NAME
- VITAL STATISTICS
- PHYSICIAN NAME
- PATIENT CONTACT INFORMATION

ENCOUNTER DETAILS — 164

- STATUS:
- DUE DATE:
- SCHEDULED: Y
- ENC. DATE:
- LAST UPDATED:

[EDIT DOSAGE] — 170

DOSAGE — 168

| DAY1 | DAY2 | DAY3 | DAY4 | DAY5 | DAY6 | DAY7 |
|------|------|------|------|------|------|------|
|      |      |      |      |      |      |      |

TEST RESULTS — 166

| DATE | MM/DD/YYYY |
|------|------------|
| TIME | HH:MM |
| TEST 1 VALUE | X |
| TEST 2 VALUE | Y |
| MINIMUM TEST 1 | X |
| MAXIMUM TEST 1 | Y |
| STATUS | OK |
| QC1 | OK |
| QC2 | OK |

CALL LOG INFORMATION — 172

[SUBMIT] — 174   [CANCEL] — 176

FIG. 10

METHOD AND SYSTEM FOR MONITORING AND MANAGING PATIENT CARE

CROSS-REFERENCE TO RELATED APPLICATION

This application claims the benefit of U.S. Provisional Application No. 61/234,420, which was filed on Aug. 17, 2009, and entitled METHOD AND SYSTEM FOR MONITORING AND MANAGING PATIENT CARE, which is incorporated herein by reference.

BACKGROUND

Diagnosis of ailments and treatment of disease often requires an analysis of biological signs obtained from a patient in the course of normal activity over a period of time. A variety of different personal health monitors have been developed to gather data related to a patients health. The particular functionality of the monitor generally depends on the condition being monitored the type of data being collected.

As one example, the current standard of care for long term anticoagulation patients (LTAP) requires periodic and frequent (up to twice a week) visits to a blood laboratory or anticoagulation clinic to measure prothrombin time (PT) and the associated international normalized ratio (INR) (PT/INR). PT/INR is a measure of blood clotting and monitoring of PT/INR values is the mechanism by which the adequacy of oral anticoagulation (e.g., with warfarin) is monitored. Patients requiring long-term oral anticoagulation therapy for a variety of clinical conditions, including atrial fibrillation, mechanical heart valves, and venous thromboembolism, require periodic assessment of the PT/INR to help ensure the degree of anticoagulation is within a therapeutic range. In one model of long term anticoagulation management, after the blood laboratory has been resulted, the results are made available (e.g., via fax or electronic medical record) to the monitoring health care provider's office for review. The health care provider then contacts the patient with results via telephone, and prescribes any changes in warfarin dose and the time of the next PT/INR measure.

SUMMARY

Embodiments of the invention disclosed herein provide a method and system for monitoring and managing patient care.

For example, a patient management system can include a patient unit that obtains results data from a patient device and provides for two-way communication between the patient unit and a remote database. The patient unit can communicate with the remote database to obtain encounter instruction data for a given encounter as well as to send response data for the given encounter. A back office system can also access the database (e.g., the database is shared and common to the back office system and any number of patient units). The back office system can retrieve the patient data for one or more patient units. The back office system can further add or modify encounter instruction data for use during a next encounter at each patient unit. The back office system can also set a dosage for the patient that can be stored in the remote database and retrieved by the patient unit as part of the given encounter. The dosage can be a quantity of something (e.g., a drug, chemical, food) that can be administered to a patient as well as can refer to a therapy or other form of treatment. The back office system may also employ a rules engine that can be programmed according to an established protocol and can automatically generate encounter instructions and dosage information for one or more patient.

According to one embodiment, a patient monitoring system can include a patient unit and a back office system. The patient unit can include a device interface configured to provide for data communication with a measurement device, the patient unit being programmed to selectively retrieve results data indicative of at least one patient condition from the measurement device. The patient unit can also include a communication module configured to provide two-way communication via a network with a remote database. The communication module can be configured to retrieve encounter instruction data for the patient unit from the remote database for a given patient encounter that includes at least one set of predetermined queries and be configured to send response data to the remote database for the given patient encounter, the response data comprising at least one of stored user responses and the results data. A user interface can present at least one of the predetermined queries to a user and receive user responses to each of the predetermined queries for the given patient encounter, the user responses for each of the predetermined queries being stored in memory of the patient unit as the response data for the given encounter. The back office system can be programmed to access the remote database and to retrieve the response data from the remote database for at least one patient unit, the back office system further being programmed to at least one of add or modify the encounter instruction data that is stored in the remote database for a next patient encounter at the patient unit.

Another embodiment provides a method for remote patient management. The method can include initiating a given encounter at a patient unit in response to a user input provided at the patient unit. A two-way wireless communication channel can be opened between the patient unit and a remote database, such that the patient unit retrieves encounter instruction data for the given encounter. The encounter instruction data defines a sequence of steps to be executed at the patient unit for the given encounter. Each of the sequence of steps is executed at the patient unit, at least some of the sequence of steps requesting responses from the user to confirm compliance with the respective step and at least one of the sequence of steps corresponding to test subroutine. The test, subroutine can also be executed at the patient unit to receive results data indicative of a patient condition. Response data for the given encounter can be sent from the patient unit to the remote database via a communication channel. Encounter instruction data can be generated for a next patient encounter at the patient unit based on the response data stored in the remote database for the given encounter, such that the encounter instruction data can be stored in the remote database for retrieval by the patient unit for a next encounter.

BRIEF DESCRIPTION OF THE DRAWINGS

FIG. 9 depicts an example of an unclosed encounter graphical user interface.

FIG. 10 depicts an example of an encounter information graphical user interface.

DETAILED DESCRIPTION

The subject innovation relates to systems and methods for remotely monitoring and managing one or more patients. Embodiments disclosed herein provide for two-way communication between a patient unit and a provider to control and manage patient encounters. Systems and methods can be programmed to help ensure and track patient compliance with a protocol that is defined by the provider. As but one example, the systems and methods can be utilized as part of an oral anticoagulation care (OAC) protocol. It will be appreciated that in other embodiments the systems and methods can be extended to other models of patient management. For example, patients requiring orthopedic rehabilitation can have activity monitored with sensors including accelerometers, joint angle, and foot force sensors. These sensors can be used to insure that a patient is within a therapeutic activity range according to an established protocol for the given patient.

Figure 1:
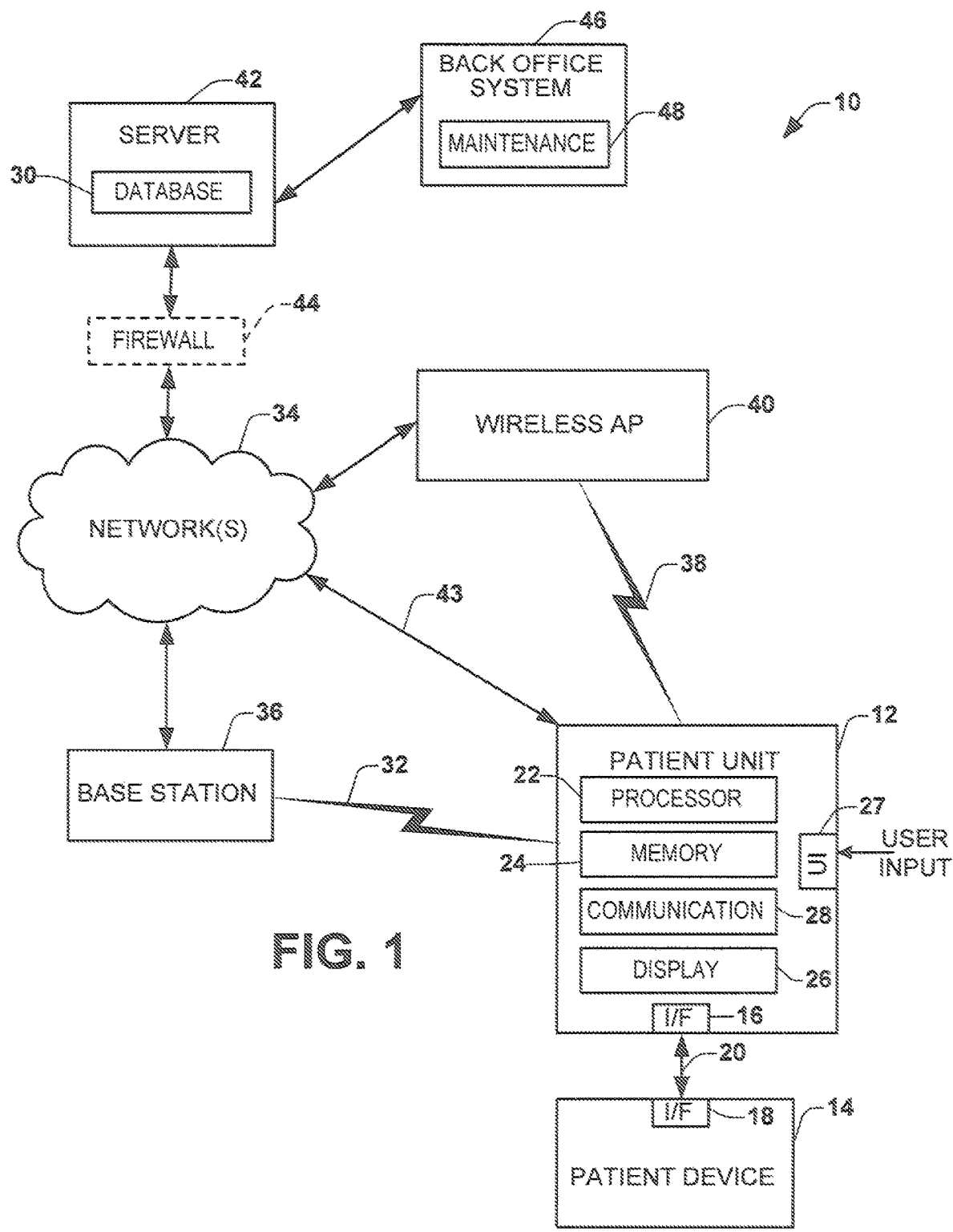
FIG. 1 depicts an example of a patient monitoring system.

FIG. 1 depicts an example of a patient monitoring system 10. The monitoring system 10 includes one or more patient units 12, each of which is programmed and configured to acquire encounter data based on patient interaction with the patient unit and patient condition. The encounter data can include responses provided by the patient to different queries in an encounter sequence as well as data obtained from an associated patient device 14. The data can be measurement data representing one or more patient physiological conditions measured by the device 14, a measurement of one or more therapies delivered to the patient via the device, an indication of patient compliance with a protocol or a combination thereof.

The patient unit 12 includes a device interface 16 that is configured to communicate with the corresponding port or interface 18 of the patient device 14. The patient unit 12 can employ the interface 16 to communicate data and commands between the patient unit 12 and the patient device 14. For example, the interface 16 and 18 can provide for communication over a communication link 20 according to a serial data communication standard (e.g., as Ethernet, FireWire, USB, RS-232, RS-485 or the like). It is to be understood that the communication link 20 between the patient unit 12 and the patient device 14 can be a physical connection, such as a bus having any number of one or more conductors, an optical fiber link, or a wireless connection such as Bluetooth, an optical wireless (e.g., infrared) link or an 802.11x link.

By way of example, the monitoring system 10 can be part of an anticoagulation monitoring system and the patient measurement device can be implemented as a prothrombin time (PT) international normalized ratio (INR) meter. For instance, the measurement device can be stand alone patient testing apparatus, such as the PT/INR INRatio monitor, which is, commercially available from Inverness Medical, Inc. of Waltham, Mass. It will be understood and appreciated that the patient unit 12 can be configured with one or more interfaces 16 to provide for communication with any number and type of PT/INR monitors as well as other types of patient monitoring and testing devices.

The patient unit 12 includes a processor 22 and memory 24 that are programmed for controlling the patient unit. Such controls can include selectively retrieving measurement data from the patient device 14. Such controls further can be implemented to provide commands or otherwise control activation and deactivation of the patient device 14. For example, the patient unit 12 can be programmed to maintain the patient device 14 in a powered off or standby condition such that the patient measurement device is inoperable to obtain the measurement from the patient until after a predetermined condition of the patient unit has been achieved. The predetermined condition of the patient unit, for example can include completing a questionnaire or a predefined sequence of questions. The questions and other instructions can be presented on a corresponding display 26 of the patient unit 12.

The patient unit 12 can include a user interface 27 which can utilize the display 26 for presenting the predetermined queries or questions to a user as part of a patient encounter. Other, means can be utilized for presenting the questions or instructions to the user (e.g., audible or tactile). The display 26 can also be implemented as the user interface, such as a touchscreen, or other means can be provided (e.g., keypad, keyboard, mouse, or the like) for receiving user inputs at the patient unit 12, such as confirmation of patient instructions and responses to questions. The questions presented via the display 26 can be retrieved from the memory 24 as part of a patient encounter. For instance, when a new patient encounter is begun by the patient, such as for a scheduled encounter, patient encounter data may be retrieved from a remote database 30. During an ensuing patient encounter, responses to each such question and confirmation of patient instructions can further be stored in the memory 24 in association with the respective questions and instructions that are presented. Those skilled in the art will understand and appreciate all various types of documents and forms (e.g., an XML document, text files) that can be utilized to store the questions and responses in the memory 24.

The patient unit 12 also includes a communication module 28 that is configured to provide for real-time communication with the database 30. The communication module 28 can be configured to provide for wireless data communication or the communication module 28 can provide for data communication over a physical connection. In the example of FIG. 1, the patient unit 12 can be in wireless communication with a server 42 through one or more networks depicted at 34.

For example, the patient unit 12 can connect with the network 34 via a first wireless link 32 through a base station 36. The base station 36 can be a cellular base station that provides cellular voice and data communication as part of a wide area network. Examples of cellular data networks include the enhanced data rates for GSM evolution (EDGE) or third generation (3G) mobile telecommunications technologies (e.g., universal mobile telecommunication system (UMTS) or GSM based technologies) as well as extensions of the third generation technologies, including 3GPP or WiMax.

Additionally or alternatively, the patient unit 12 can wirelessly communicate with a wireless access point (AP) 40 via a second wireless link 38. The wireless AP 20 can communicate with the server 42 through the network 34. As another alternative, the patient unit 12 can communicate with the server to access the database 30 through a physical link 43, such as by the communication module 28 implementing a modem for data communication via public switch telephone network (PSTN) or a cable modem.

The connection between the server 42 and network 34 can be direct or alternatively through an optional firewall 44. It will be understood and appreciated that the communication module 28 of the patient unit can operate according to any one or more of these communication technologies, which may vary according to application requirements and availability of such data communication services to the patient-user of a given unit 12.

After the patient encounter, the communication module 28 can send patient encounter response data to the database 30 via the appropriate data path. When data is being sent from the unit 12, a message can be presented on the display 26, such as "Data Sending . . . Please wait." Additionally, in certain circumstances such as an alarm event (e.g., corresponding to an off-nominal response being entered by the user at the patient unit 12), the communication module 28 can send response data or other information to the database 30 prior to completion of a patient encounter. Alternatively or additionally, the patient unit 12 can send an alert in other forms, such a voice message, email message, text message, or pager message to one or more pre-identified recipients. The specifics of how and when and under what circumstances the patient unit 12 can contact the database or otherwise alert the caregiver can be programmed according to a set of programmable rules or logic stored in memory of the patient unit. The rules or logic further can vary for each patient unit according to the needs of a given patient as well as the requirements of a respective caregiver.

The patient encounter response data can include the user responses that have been stored in memory 24 in response to user inputs via the user interface 27 as well as measurement data that has been obtained via the device 14. Additionally, the encounter response data that is sent to the database 30 can also include the set of predetermined queries that were presented to illicit the responses made to the user. That is the encounter response data that is archived in the database 30 can include both the questions and corresponding responses to facilitate review by a caregiver.

The database 30 can be configured to store the patient encounter data, for each of a plurality of patient units 12. The data can be stored in the database 30 for each of any number of encounters, each of which can be specified by a unique encounter identifier (e.g., a number or other value) for each patient unit 12. Each patient unit 12, for example, can access a predefined location in the database (e.g., an SQL database) 30 for storing the encounter response data. For example, each patient unit 12 can be programmed to connect to one or more network locations, such as a URL, to which the communication module 28 sends response data during or after each encounter is completed or in response to an alert condition being triggered.

Each patient unit 12 can be programmed with a unique unit identifier (e.g., a serial number) that is stored in volatile memory of the respective patient unit. The unit identifier can be linked or otherwise associated with a patient identifier via a back office system 46. Alternatively, the unit identifier can be linked to patient identifier in the database 30. The patient identifier can include a unique patient code or sequence of values, the patient's name or any combination of information that can be utilized to identify a patient within a given institution.

The data communicated between the patient unit 12 and the database 30 identifier does not include patient identifying information, such as to comply with federal and local regulations. To provide for additional security this data communication between the patient unit and the database can further occur over an encrypted data communication channel (e.g., SSL encryption). The patient unit thus can operate as server that stores the data in the database 30 for use by a back office system 46 that is operated by the caregiver. As a further example, the stored data can include date and time of the encounter as well as the time of all key communications and patient interactions (e.g., questionnaire started, INR value sent), PT/INR readings, and answers to all questions asked via respective patient units 12, and associated serial numbers for PT/INR readers and consumable test strips per reading. Each encounter at the patient unit 12 can thus result in the patient unit storing an arrangement of various types of information in the database 30, which can be evaluated by a caregiver via the back office system 46.

The back office system 46 can be is programmed to retrieve and manage patient data from the database 30 for each of a plurality of the patients. The back office system 46 can be implemented on one or more computers locally or run as an application on a network server as is known in the art. Due to potential sensitive of nature of health care information, the back office system typically will run behind the firewall 44.

The back office system 46 can be programmed to enable a caregiver to manage and view patient encounter information for each patient unit. Associated with each patient unit 12 can be other patient personal information, such as name, ID number, medical history information or the like. As mentioned above, this' patient information that can be stored in the database 30 or otherwise accessible by the back office system, such as from an electronic medical record (EMR) system.

After the patient encounter response information has been reviewed by a caregiver, the caregiver can employ a user interface to select instructions that can be stored in the database and sent to the patient unit 12. The instructions can be dosage instructions, such as for one or more drug therapy, physical therapy or other actions that may be directed by the caregiver for a given patient. Additionally or alternatively, the set of predetermined encounter questions and instructions for each given patient unit 12 can be modified, which can be done automatically based on rules/algorithms implemented in the back office system 46, manually by the caregiver or as a combination of manual and automatic methods. The questions and instructions can be stored in the database 30 as patient encounter instruction data.

The patient unit 12 can retrieve the caregiver instructions from the database at the end of encounter. The patient unit can request confirmation of the instructions (e.g., dosage instructions) via the user interface 27. Each time changes may occur in dosage, frequency of testing and instructions associated with a patient encounter, logic implemented at the patient unit 12 can acquire confirmation via the user interface 27 to ensure that instructions have been received and that they are understood. In this way, the caregiver can manage patient behavior as well as ensure compliance with a patient-specific or generalized protocol, including dosage and testing procedures.

In one example embodiment, the system 10 can be implemented to provide an Oral Anticoagulation Care (OAC) remote monitoring system that provides an OAC clinic, physician practice, or larger medical institution the ability to provide a remote, automated, and real-time virtual OAC practice. The system 10 further provides two-way communication between a caregiver via the back office system 46 and the patient via the patient unit 12. As a result of substantially real-time communication through the network(s) 34, the system 10 enables confirmation of instructions and procedures with automated compliance authentication, with caregiver control of patient interaction, scheduling and maintenance. Additionally, the system 10 allows for a protocol to be uniquely tailored to specific patient needs by allowing the caregiver to vary the time interval between "patient encounters," and also customizing queries made of the patient, such as part of a questionnaire. For instance, the back office system 46 can generate custom inquiries for a given patient automatically or manually entered by the caregiver, such as based on preliminary encounter response data provided by the patient unit 12 to the remote database 30. The unique inquiries and other customization can be generated and sent as encounter instruction data to the patient unit. The encounter instruction data can be generated, for example, either based on the response data for the current "encounter" or based on analysis of data from one or more previous encounters. For example, a particular response received in response to a question presented on the display 26 about bleeding may trigger a branch of questioning of the primary set of questions. Lastly, the encounter sequence can be unique for each patient based on history, or preexisting conditions of the patient-user.

For the example of implementing an oral anticoagulation care (OAC) remote patient management protocol with the system 10, a series of rule based steps (referred to as sequence steps), which define an encounter, can be implemented via the two-way real time communication that exists between the patient unit 12 and the back office system 46. The encounter begins by the patient unit 12 retrieving an updated set of questions in response to the user initiating the encounter. Once the updated data has been received and stored in local memory 24, the patient unit can present the patient a series of mutually exclusive questions (e.g., presented on the display 26). After the sequence of questions has been completed, then the patient is asked to check their PT/INR as part of test subroutine. These questions and the test results are used to drive a process relationship. The process then walks through each interaction as a step. Each step can represent a conditional relationship that will require the process to divert into a branch process of the programmed encounter. Each branch process can itself divert into any number of new branches, therefore the process can be current as well as have any number of exit points.

An example sequence for implementing interactive patient remote care are as follows:
10. Patient unit 12 accesses remote database 30 for retrieving encounter instruction data and storing such data in memory 24. The encounter instruction data can include OAC questions and logic to control queries presented to the user.
20. Patient utilizes user interface 27 to answer OAC specific questions presented on display 26 (Post Scheduled PT/INR measurement Cue). Responses are stored in the memory 24.
30. Confirm OAC questions. After completing the OAC questions, the patient unit 12 automatically communicates with the remote database 30 and sends encounter response data that includes answers to questions as well as the questions.
40. Patient unit 12 controls measurement device (PT/INR monitor) 14 via the communication link 20. The patient unit 12 also controls dosage schedule to be ready for testing post confirmation of receipt from caregiver. Such control is based on programming stored in memory 24 and can be adjusted based on the encounter instruction data retrieved from the remote database at the beginning of the sequence.
50. After confirming responses, the user follows PT/INR meter instructions presented on the display 26 of the patient unit for performing PT/INR test on the device 14.
60. The user employs the user interface 27 to confirm completion of test and provide patient specific code to authenticate measurement compliance.
70. Patient unit 12 automatically communicates measurement information to caregiver via the networks) 34. The patient unit 12 can send the measurement information as encounter test data. The test data is stored in the database 30 as part of the encounter data, which can also include the response data already sent by the patient unit.
71. Data from INR encounter and patient specific database can be utilized to determine appropriate dosing schedule (an instructed automatic process and/or manual process by the caregiver).
80. Back office system 46 communicates dosage schedule to database 30, which is retrieved by the patient unit 12. The dosage schedule can be presented on the display 26 or other output device. Other messaging can also be utilized as a back-up (e.g., an automatically generated email, text message or the like).
90. User employs user interface 27 to confirm receipt of the dosage schedule for the next week or other time period defined by the caregiver. The dosage schedule can also define a time period (e.g., a day or other time period) for when the next encounter is scheduled.
100. Patient unit 12 automatically communicates authenticated confirmation of dosage schedule back to remote database, which can be monitored (by the back office system 46 and/or by the caregiver) and utilized to close the encounter—assuming no off-nominal responses or other information was received during the encounter. Thus, the two-way communication can be used to ensure compliance with the protocol.
110. Patient unit 12 is recycled for next encounter or question/testing sequence, which can be set by the scheduling information provided with the dosage schedule.

For the example where the patient monitoring device is for monitoring long term anticoagulation therapy, sample sequence of questions that can be presented to the patient via the display 26 as part of a patient encounter can include the following questions listed as 1-8. In response to each presented question, a patient can enter a response, yes or no, via the user interface 27.

| Question Since your last INR check... | Response | |
| --- | --- | --- |
| 1. Have you been hospitalized or treated in an emergency room? | Y | N |
| 2. Have you experienced any bleeding | Y | N |
| 3. Have you had any falls or injuries? | Y | N |
| 4. Have you missed any doses of Coumadin? | Y | N |
| 5. Have you taken any extra doses of Coumadin? | Y | N |
| 6. Have there been any changes to your medications (prescribed and over the counter)? | Y | N |

-continued

| Question<br>Since your last INR check... | Response | |
|---|---|---|
| 7. Have you made any significant changes to your diet? | Y | N |
| 8. Are you scheduled for a medical procedure that can require stopping your Coumadin? | Y | N |

Additional information from a subsequent branch questions can be triggered in response to a positive response to one or more questions. For instance, branch questions for possible inclusion following an off-nominal, positive response to question (7) above can include questions requesting information about fasting for medical tests or procedures, poor nutrition due to illness, or change in your intake of vitamin K-rich foods. Thus, a set of response data that includes one or more off-nominal responses can include a greater amount of data and information than a data set for an entirely nominal set of responses.

Additionally, if any protocol questions are answered yes (e.g., off-nominal), the patient unit 12 can automatically alert the patient to contact the caregiver. Alternatively, after reviewing the off-nominal response information, the back-office system 46 can issue a request to contact the patient. The patient contact can be made by automatically sending a message for retrieval by the patient unit 12. Alternatively, a cellular voice interface of the patient unit (corresponding to the communication block 28) can be utilized to initiate a telephone call from the patient unit 12 to a predefined telephone number for a caregiver, such as a nurse's station at a Coumadin clinic. As another example, the caregiver contact the patient directly via various other communication methods, such as disclosed herein (e.g., email, texting, paging or the like).

Alerts can also be provided to the user via the display or other output device during the patient encounter. The user interface 27 can be utilized to confirm that the patient has received and understood a given alert. This confirmation of the alert can further be stored in the memory 24 as part of the response data. Confirmation of a given alert by the user can be required before allowing further action in the encounter sequence. That is, the unit may remain in a loop waiting for the confirmation from the user and even return to this same confirmation request should the unit time out before the confirmation is received. The confirmation can be utilized to ensure that the corresponding instructions have been received and understood by the patient. Responses to each of the questions, instructions and alerts can be automatically sent to the remote database 30 as response data, as described herein.

As mentioned above, after data is gathered at the patient unit, the unit relays information to the caregiver, which can be accessible via the back office system 46. For instance, the back office system 46 can implement a rule based process and present patient data so that the caregiver can make all necessary judgment/care decisions and oversight of dosage or therapy algorithms dependent on patient condition. This may include adjusting dose or therapy, changing testing interval, scheduling a face-to-face encounter, or advising the patient to seek medical attention. For example, the back office system can be programmed to implement a process based "Coumadin practice" protocol that can change caregiver actions and rules based on individualized care. As described herein, OAC specific rules can be added, modified or deleted to provide for specific needs or changes in remote based protocols as new protocols or additional items are identified to either provide better outcomes or system efficiencies. Rules can be automated to present suggestions to the caregiver, which can be manually accepted by the caregiver as is or can be modified by the caregiver.

The back office system 46 also includes a maintenance component 48 that is programmed for adding, updating, modifying and viewing information stored in the database 30. The maintenance component 48 can implement automatic processes and rules for controlling what data is stored in the database 30 and provided to each patient unit 12. Alternatively, or additionally, manual confirmation or authorization from one or more designated caregiver can be required for certain changes, which can be programmable. The maintenance component 48 can include a variety of security levels requiring different levels of authorization depending upon the caregiver's relationship with the patient. For example, a physician can have a higher level of authority and therefore modify a greater number of entries than a nurse or other caregiver who may be utilizing a system. According to one embodiment, manual input from a caregiver may be required in order to modify a dosage, change a testing interval or otherwise modify a treatment plan for a given patient, which can be stored in the database 30 as part of the encounter instructions data for a given patient unit 12.

The back office system 46 can be programmed to include one or more application that provides means for electronic patient scheduling of remote care, data capture and communication, confirmation of OAC care steps and confirmation of compliance to OAC care protocol. The back office maintenance component 48 for controlling the patient management system can be either resident in the remote database 30 and accessible through the web application or resident within a separate server (not shown).

The maintenance component 48 and other applications associated with the back office system 46 can run on one or more computers locally or the maintenance component can be utilized via the corresponding network connection. It will be understood and appreciated that it could be any number of instances of the back office system 46, which may run on different work stations within the system 10. The caregiver interface implemented by the back office system 46 can allow for the caregiver to not only see final process results, but also to audit the process to see (e.g., in real time) at which step of the process the patient is at for compliance information and status of the individual patient remote encounter. The caregiver interface can be customized to the caregiver by the caregiver.

In view of the foregoing, it will be appreciated that the system 10 provides an architecture that can implement a rule based patient care, real-time management system that employs two-way communication. It is to be further appreciated that the device 14 is not limited to PT/INR information and can be implemented to provide more than one type of measurement information. For instance, the patient device 14 can provide information about blood pressure, temperature, heart rate or the like in addition to other testing that can be performed on the patient's blood. Additionally, while a single patient device 14 is illustrated in FIG. 1 and as being separate from the patient unit 12, there can be any number of measurement devices which may be separate or which may be integrated within the patient unit 12 as modality specific circuitry, such as shown and described in each of the following copending U.S. patent applications: U.S. patent application Ser. No. 11/236,899, entitled COMPACT WIRELESS BIOMETRIC MONITORING AND REAL TIME PROCESSING SYSTEM; U.S. patent application Ser. No.

11/686,667, entitled TRANSFER FUNCTION CONTROL FOR BIOMETRIC MONITORING SYSTEM AND RELATED METHOD; and U.S. patent application Ser. No. 12/051,019, entitled DATA ACQUISITION FOR MODULAR BIOMETRIC MONITORING SYSTEM, each of which applications are incorporated herein by reference.

Figure 2:
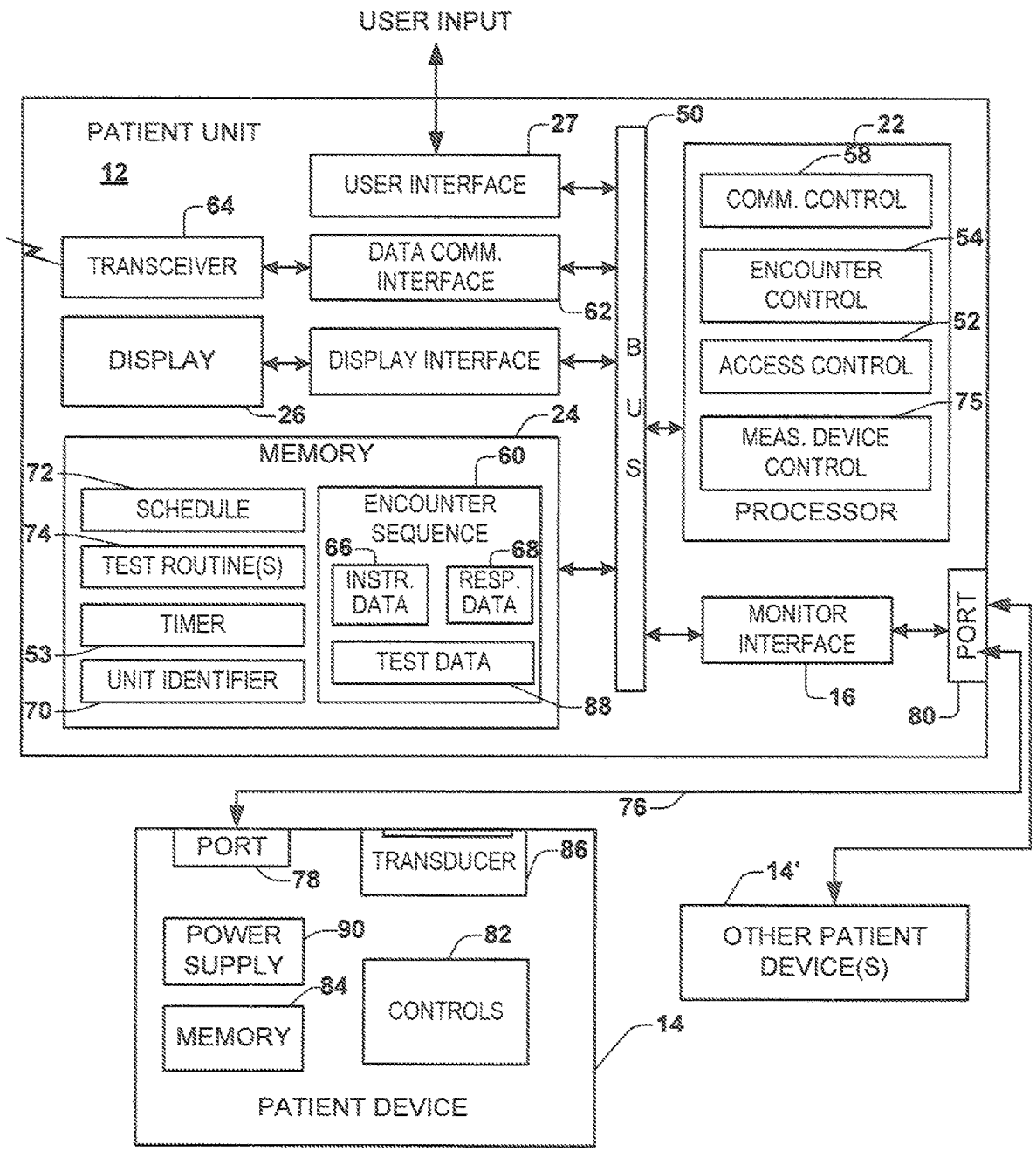
FIG. 2 depicts an example of a patient unit connected with a patient measurement device that can be used in a patient monitoring system.

FIG. 2 depicts an example of a block diagram of a patient unit 12. In the example of FIG. 2, the patient unit 12 includes a processor 22 that is coupled to the memory 24 via a bus 50. The processor 22 can implement a variety of control functions for controlling the patient unit and communication relative to other devices within the patient monitoring system. In the example of FIG. 2, the processor 22 executes an access control component 52 that can be programmed to control access to various functionality implemented by the patient unit 12, including therapy and dosage dispensing control.

The access control 52, for example, can be implemented as a locking or control function that restricts access to the functionality of the patient unit 12. For instance, the access control can require a passcode that can be entered via user interface, which may be implemented as including a keypad, a microphone, a biometric scanner or other mechanism (e.g., software/hardware key) that can be utilized to provide secure access to the patient unit 12. After the passcode has been entered or the user has otherwise been authenticated by the access control 52, available options can be presented on the display 26. The options can include a variety of setup options (e.g., change passcode, lock system, or begin scheduled encounter).

A timer function 53 stored in memory 24 further can automatically lock the unit 12 if the unit has not been used (e.g., no interaction via the user interface 27) within a predetermined time period (e.g., five minutes). The timer function 53 can be utilized at any time, including during an encounter sequence that has already been initiated. Access to the unit functionality can be made available once again in response to the user re-entering the requisite passcode. If the time unit locks out the unit during an encounter due to lack of user interaction, the unit can resume the encounter sequence at the step where it left off when the unit locked out. Alternatively, the encounter can start over at the first step of the encounter sequence. The manner in which the process is resumed can be defined by the caregiver and implemented as part of the access control function 52. For example, the timer function 53 can be programmed with one or more function to execute if a timeout condition occurs (e.g., If timeout=Y, Do Timeout_function_1).

The processor 22 can employ an encounter control 54 to control what information is presented via the display 26. The encounter control 54 thus can include executable instructions that control a patient encounter, such as by selectively presenting a sequence of questions and instructions in a predetermined order to a user via the display 26. The user can employ the user interface 27 to provide appropriate responses to the questions and confirmation instructions that are presented. The particular sequence of questions and instructions can be programmed uniquely for each patient unit, retrieved from a remote database and stored in the memory 24. Alternatively or additionally, a set of default questions can be stored in the memory 24.

By way of example, at the beginning of an encounter and in response to being initiated by the user via the user interface 27, the encounter control component 54 can employ the communication control 58 to retrieve encounter instruction data 66 from the remote database 30. The encounter instruction data 66 can be stored as part of encounter sequence data 60 in the memory 24. For instance, the communication control 58 can be configured to send corresponding command to a data communication interface 62 via the bus 50 for initiating a communication session. The data communication interface 62 can convert the command to an appropriate format for sending to the remote database via a corresponding transceiver 64. It is to be understood that the patient unit 12 can include any number of data communication modules each of which can include a corresponding transceiver 64 and communication interface 62 for providing two-way data communication according to a respective communication protocol.

As described herein, the transceiver can be implemented as a wireless transceiver or can be implemented to communicate via a physical connection, such as through the land line of the PSTN. Thus, the patient unit 12 can employ the communication interface 62 and transceiver 64 to send data and instructions to the remote database as well as to retrieve or receive information from the remote database. In one embodiment, each patient unit 12 operates as a server in the patient management system that is programmed to store and retrieve data from the remote database.

As part of the request for the encounter instruction data 60, each message from the patient unit 12 can uniquely identify the patient unit, such as by a unit identifier (ID) 70. The unit identifier 70 can be a serial number or other unique identifier to help identify the source of the information communicated to and from each patient unit. The unit identifier 70 can be a set of characters stored in the memory 24 such as can be hard coded by the manufacturer (e.g., a serial number) or it may be programmable by the back office system. Mapping (e.g., via look-up table) can be performed in the remote database to associate requests and responses from the patient unit 12 with a given record, such as a patient record from an EMR system. Thus, data received from a given patient unit 12 can be unambiguously identified to the given patient unit, and only within the caregiver's interface is the data associated with a patient by patient ID or name.

The encounter instruction data 66 can be updated for the patient unit 12 each time the user initiates a scheduled encounter sequence. For instance, encounter schedule data 72 can be stored in memory 24 to indicate when a next encounter is to begin. The schedule data 72 can be set after the patient unit 12 sends response data 68 to the remote database. For instance, the encounter schedule data 72 can be retrieved from the database via the transceiver 64 along with dosage information, such as described herein. The specificity of the schedule can be set to a time and date according to protocol established for a given patient or group of patients. Thus, if the patient initiates an encounter during the scheduled time period (e.g., a day or a time window within a predefined day), the encounter control 54 can employ the communication control component 58 to retrieve instruction data 66 from the remote database. As a result, the encounter control 54 can employ the updated instruction data 66 for presenting the predetermined set of queries and other instructions to the user via the display 26. By updating the encounter instruction data 66 when a new encounter is initiated allows a substantially real-time control of the patient encounter by the caregiver. This way, if any changes have been made in response to a preceding encounter response that was submitted, updated queries and other relevant instructions can be provided to ensure appropriate care for the patient user.

As each question is presented on the display 26, appropriate responses are entered via the user interface 27 and stored in the memory 24 as encounter response data 68. The encounter response data 68 and the queries that were provided as part of the encounter instruction data 66 thus can be combined to define an encounter sequence 60 that is stored in the memory 24. Alternatively, the encounter responses can be otherwise associated with the questions (e.g., by a question identifier or code) at the remote database. After the encounter control 54 has determined that the encounter is completed, which can be after patient measurement data has been obtained from the patient device 14, the encounter control can employ the communication module 58 to send the encounter response data 68 and/or the entire encounter sequence from the memory 24 to the remote database through the communication interface 62 and transceiver 64.

As part of the encounter, the encounter control 54 can also provide for the control and retrieval of measurement data from the patient device 14. For instance, the encounter sequence defined by the instruction data 66 can include a call to one or more test subroutines 74. The test subroutine 74 can include instructions executable by the processor programmed to control and retrieve information from the patient device 14. As one example, the encounter control 54 can employ a measurement device control 75 that is pre-programmed to control operation of and communicate with the patient device 14.

In the example of FIG. 2, the patient unit 12 is connected to the patient device 14 through a connection 76 between respective ports 78 and 80. The particular type of connection 76 will depend largely upon the type and configuration of patient device 14 and its available communication means. For instance the patient unit can include a connector port 78 for an output device (e.g., a printer port) and the interface 16 of the patient unit can be configured to receive output from such port as well as to control the device 14. The patient unit 12 can be configured to adapt a variety of different types of patient measurement devices. This can include standard or proprietary types of connections, included physical connections and wireless connections, such as described herein. Thus, it will be appreciated that the device 14 is not required to be designed for use with the patient unit 12, but the patient unit can be configured to automatically retrieve results data from the device 14 via existing connections and ports.

In one embodiment, the measurement device control 75 sends appropriate commands through a monitor interface 16 that is coupled with the port 76 for instructing the patient device 14 to enable the device, such as to power-up or otherwise activate the device. Alternatively, the command can be implemented providing the command to maintain a power off or sleep mode for the patient measurement device until an appropriate time within the encounter sequence, as dictated by the encounter control 54. In this way, the patient unit 12 can use the communication through the connection to selectively activate and deactivate the measurement device to help ensure the user's behavior complies with the protocol.

As an example, the encounter instruction data 60 or the encounter control 54 can maintain the patient device 14 deactivated or disabled until after a predetermined set of one or more queries, as provided by the encounter instruction data 60, have been answered or the encounter control determines that the unit is otherwise ready for receiving patient measurement data. In this way, certain preliminary information can be collected before the patient can perform testing. For instance, by selectively disabling/enabling the patient device 14, there is a reduced likelihood that patient's answer/response will be influenced by an otherwise premature measurement that may be acquired via the patient device 14. Those skilled in the art will understand and appreciate various ways that patient measurement device can be deactivated or otherwise be prevented from allowing a patient perform a measurement until enabled by the measurement device control 75.

After the patient measurement device has been enabled or otherwise activated, instructions can be provided to user, such as via the display 26 or other output device (e.g., a speaker) advising the patient to perform the appropriate test or tests. The type of test and procedures for implementing the test can vary according to the specific type of measurement device (or devices) 14 being implemented. The instructions along with program code for controlling the device 14 can be stored as part of the test subroutines 74 in the memory 24. Additionally, the back office system can manually or automatically update the test routines 74 changes in a test protocol as well as to accommodate new or different test devices as part of the encounter sequence. These updates can be implemented outside the constraints of an encounter initiated by the user.

In the example of FIG. 2, the patient device 14 can include a set of controls 82 that are programmed and/or configured to control operation of the measurement device. The controls 82 can include providing instructions and controlling a corresponding display (not shown) of the measurement device. Additionally or alternatively, the controls 82 can be programmed or configured to perform calculations such that the measurement information that is stored in memory 84 is normalized or provided in a format suitable for presentation to a patient. The patient device 14 can also include a one or more transducers 86 that can be configured to convert a sensed condition into a corresponding electrical signal having a value. This value can be converted by the controls 80 to the measurement data that is stored in the memory 84. The specifics of the patient measuring device 14 will vary according to the type and configuration of the device. As described herein, the patient unit 12 may be utilized with (e.g., to control, obtain test data and/or both) a variety of different patient devices, such as can include monitoring device as well as therapy/dosage dispensing and control devices, as appropriate for a given patient condition.

The patient unit 12 can be programmed to determine that the test or measurement has been completed. Alternatively or additionally, as part of the encounter sequence, the patient unit can present a query to the user (e.g., via the display or other output) to confirm when the test has been completed. After the unit has determined that the test has been completed, the patient unit 12 can acquired test results data from memory 84 of the device along with temporal information (time and date). This measurement data can be retrieved from the memory 84 (or received as an output generated by the device 14) via the port 76 and stored as part of the encounter data 60, such as test data 88. The encounter control 54 as part of the encounter can employ the communication control 58 and sending the test data 70 to the remote database via the transceiver 64. For instance, the patient unit can send the measurement data as a text file or it may be otherwise encoded as data in a predetermined format for storage in the remote database.

While the example of FIG. 2 has been described in the context of one patient device 14, it will be appreciated that there, can be any number of one or more other patient devices 14'. The patient unit 12 thus can be programmed with subroutines 74 to enable communication with each respective patient device for obtaining corresponding measurement data. The appropriate subroutines can be programmed in a given encounter sequence, which (as mentioned above) can be retrieved from the remote database in response to a user initiated and scheduled encounter. The types of devices 14 and 14' utilized, for a given encounter and the frequency of their use further can be selected by the caregiver. Examples of other test devices 14' include: a weight scale, a glucose monitor, blood pressure device, heart rate sensor, accelerometer, range of motion sensors, a muscle strength measurement device, a breathalyzer, or any other device that can measure one or more condition or deliver a treatment or a therapy.

It will be appreciated that a given patient device 14 and 14' can include any number of one or more sensors for sensing corresponding patient conditions, such as including but not limited to those sensors disclosed in the above-incorporated U.S. patent applications (e.g., to sense conditions relating to electromyography (EMG), electrocardiography (ECG), electroencephalography (EEG), plantar pressure, joint angle, pulse oximetry, blood pressure, core body temperature, blood levels, blood coagulation, cardiac rhythm, or other conditions). Additionally or alternatively, a given patient device 14 and 14' can be configured to control a dosage, such as can include administering a treatment (e.g., chemical or electrical), delivering a therapy (e.g., physical therapy), controlling patient behavior, and/or otherwise ensuring patient compliance with a protocol.

As an example, a given patient may be required to weigh themselves via an electronic scale measurement device daily and conduct a PT/INR test weekly. Thus, a daily encounter sequence can be programmed to instruct the user accordingly to answer a series of questions and then weigh the user, which weight can be acquired automatically by the patient unit 12 as part of executing a test routine 74 called by the encounter control 54. Alternatively, the user may manually enter his/her weight on a keypad provided by the user interface 27 of the patient unit 12 at the desired frequency as part of the daily encounter sequence. Once a week, the same user-patient can be instructed as part of an encounter sequence to conduct a PT/INR test. Those skilled in the art will understand and appreciate other types of tests or combinations of tests that can be implemented with the patient unit 12.

Figure 3:
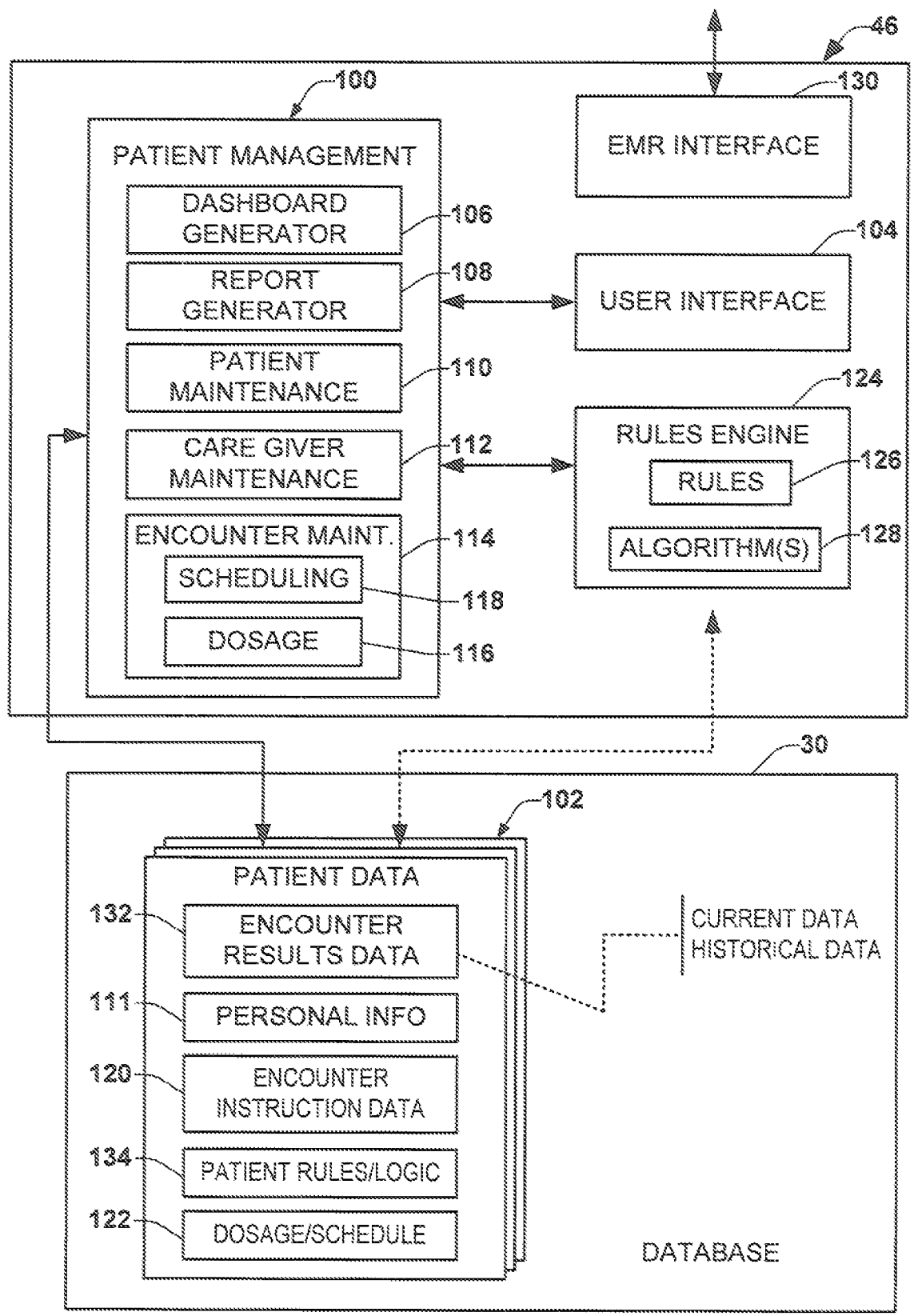
FIG. 3 depicts an example of a back office system.

FIG. 3 depicts an example of a back office system 46. In the example of FIG. 3, the back office system 46 includes a patient management module 100 that is programmed for generating and manipulating forms and graphical user interfaces as well as for updating, adding, editing or otherwise performing maintenance on information contained in patient data records 102. The back office system 46 includes a user interface (e.g., a graphical user interface) 104 that is utilized to access and manage the functionality of the patient management module 100. It will be appreciated that the patient management module 100 can employ a set of functions or methods, some (or all) of which can be accessed from multiple screens.

In the example of FIG. 3, the patient management module 100 can include a dashboard generator 106. The dashboard generator 106 can be utilized to selectively present information in forms based on the patient data 102 for any number of one or more patients. An authorized user thus can access selected information from the patient data 102 and manipulate such data via the user interface 104. The dashboard generator 106 can be used by a caregiver to gauge information about a patient's health condition based on current and/or historic patient data, such as can be sent from a patient unit as described herein over a period of time.

For example, the dashboard generate can display data in queues. These queues can include: "New Results", "Delinquent Results", and a queue of "Unclosed Encounters" for each of a plurality of patients. All queues presented in the dashboard can be sortable based on information presented in respective columns, such as via the user interface 104. The information presented in the queues can also be alarmable (e.g., able to trigger alarms based on predefined rules), which can be set via the user interface 104.

By way of example, FIG. 9 depicts an example of graphical user interface 150 based on a queue of "Unclosed Encounters" for a group of patients. As shown in this example, the GUI 150 can list information for each unclosed (or open) encounter, including a due date, patient name, test results if known (e.g., PT and INR values), a status of the encounter (e.g., by identifying the last completed sequence step in the encounter), the patient's doctor as well when the information was last updated. Alert status of an encounter can also be depicted in the user interface, such as by different colors or highlighting of the encounter data for a given patient.

As a further example, the back office system 46 can allow for determination and setting of one or more critical threshold values (e.g., PT/INR value) above which an alert is triggered. The PT/INR measurement alarm ranges can be set by the caregiver user via the user interface 104. For instance, the alarm ranges can be standardized or customized on a per patient basis. The alerts can take various forms, such a scan include sending a message, flagging a patient record, changing the color of displayed information in one or more queue in the dashboard or the like. The form of alert vary can thus be programmed for a given caregiver or institution.

A caregiver user can employ the user interface 104 to select and provide corresponding functions, such as adding a new appointment or editing an existing appointment for a given patient. The caregiver-user can also view and edit schedule for a given patient's scheduled tests, such as a PT/INR test schedule.

The patient management module 100 can also include a report generator 108 that can be utilized to generate corresponding reports based upon the patient data 102. The patient data 102 can be acquired and stored in the remote database 30 as described herein. The reports can be used to identify trends or otherwise by the caregiver or analysis can be automated. The reports can display text, graphics or a combination of text and graphics. The report generator 108 can provide a variety of constraints that can be selected and set by the user via the user interface 104 to filter and determine what portions of the patient data 102 will be included in the report being generated.

The patient management module 100 can also include a patient maintenance component 110 and a caregiver maintenance component 112. Each of these maintenance components can be utilized to create and maintain patient records or caregiver records that are utilized in the back office system 46. Such maintenance can include creating, editing, deleting or otherwise sorting/filtering through the variety of records utilized in the back office system 46. Actions and controls can also be implemented as part of the patient maintenance, such as can include flagging reminders to schedule an appointment(s). Appointments may include in-clinic appointments or telephone consultations. The patient maintenance component 110 can also be used by the caregiver for setting one or more dosages, updating encounter schedules for each patient or for a group of patients as well as creating or updating personal information for the patient. The personal information for a given patient can be stored or maintained in the patient data 102 as personal information data 111.

As a further example, the patient management module 100 can also include an encounter maintenance component 114. The encounter maintenance component can be utilized to view, edit or modify an open encounter, or otherwise obtain information about certain aspects of an encounter sequence for one or more selected patients. For instance, the encounter maintenance component 114 can be used to create or edit an encounter. This may involve changing the order of an encounter sequence, changing (e.g., add or delete) the steps in a given sequence (e.g., one or more tests), setting the questions and interactions to be presented to the patient or any combination thereof. The sequence of steps and logic for a given encounter sequence, for example, can be stored as encounter instruction data 120 within the patient data 102 for each respective patient.

The encounter maintenance component 114 can also include a dosage function 116 and an encounter scheduling function 118 to facilitate generating an encounter sequence for a given patient. The dosage function 116 can be programmed to generate a next dosage for a given patient, such as can be automatically generated based on one or more previous dosage schedules and based on the current set of test results. The dosage function 116 can require manual confirmation of the dosage by the caregiver as well as require review of selected patient history (e.g., prior test results and prior dosage) before allowing the dosage to be stored in the patient data. Additionally or alternatively, a caregiver can modify a proposed dosage, via the user interface 104. In some cases, a caregiver may be required to manually enter a dosage for a patient, such as in the event one or more alarms had been triggered in response to the patient's test data or the response data for one or more previous encounters. The dosage can be stored as dosage/schedule data 122 in the patient data 102 to be retrieved by the patient unit as part of an open encounter, such as described herein. Additionally, the dosage function 116 can employ a rules engine 124 to generate the dosage according to rules established for a given protocol, which can be a global rules or individual rules for a given patient.

The scheduling function 118 can be utilized to schedule one or more patient tests to be performed as part of a given encounter. The scheduling function can also set a time window (e.g., a day or a number of hours) during which a patient is expected to complete an encounter sequence. The schedule data provided by the scheduling function can be stored as part of the dosage/schedule data 122 that can be retrieved by the patient unit as part of an open encounter.

Another aspect of patient maintenance may be a telephone call encounter, such as can be initiated by the patient (in response to instructions presented on the display of the patient unit) or initiated by the caregiver (in response to an alarm or alert being triggered). Details of the call can be logged in to the database via an encounter form, which can be stored as part of the patient data 102 in the database.

The back office system 46 can further include a rules engine 124 that is programmed for determining how information is presented and what actions may be performed in response to the application of the set of rules 126. The rules engine 124 can also include one or more algorithms programmed to execute actions based on the rules 126. The rules 126 and algorithms 128 can be provided according to a protocol or set of protocols that are to be implemented by the system. It is to be understood and appreciated that the rules 126 and algorithms 128 can be implemented on a patient-by-patient basis such that different rules and corresponding algorithms can apply to each patient according to their particular needs and conditions. Alternatively or additionally, rules 126 can be applied on a global scale to all patients or to a group of patients.

As one example, the rules engine 124 can include a dosage algorithm 128 for adjusting patient dosages or otherwise providing a recommendation for a dose requirement based upon a historical evaluation or analysis or trends of the corresponding encounter response data for a given patient. Rules 126 can also be utilized for controlling how information is presented to a caregiver via the back office system 46. For instance, rules can be utilized to color code or otherwise flag (e.g., bold text or different fonts) encounter data that is determined to be off nominal or otherwise satisfying or failing to meet predefined conditions that are defined by the rules 126.

The rules 126 can be protocol specific rules for patient management allowing patient specific flags to be set in the patient data 102 for therapeutic ranges and other flags for specific drug interaction cautions or concerns due to specific patient needs. The environment and rules 126 are adaptable to expand to other patient care requirements and protocols. For example, where the patient unit is configured to monitor multiple patient parameters, the rules 116 can be employed to implement logic and inferences to set flags and update status information based on an evaluation of the set of patient parameters being monitored.

The rules engine 124 can also support individualized/personalized patient algorithms 128 and rules 126 based upon variables and parameters from the database 30, which can include historical data captured as the system learns unique interactions and symptoms during the remote care. As a result, the rules engine 124 can be programmed on a patient-by-patient basis for individual optimization of dosage schedule and interaction. For the example of an OAC management system, the rules engine 124 or other application can be programmed to personalize anticoagulation dosing schedule algorithms/protocols 128 based upon extrapolation/interpolation and analysis of time based changes from a given patient's data 102.

The system architecture and application allows individualized automated/remote patient management in line or the ability to provide personalized medicine protocols and a tailored patient management approach. It is envisioned that extrapolated dosage schedules and dosage can be tailored for identifying off-nominal conditions and for situations where interactions may be detected with other medications. Quality metrics and protocols can be established and encoded within the rules 126 to allow caregivers to establish quality assurance goals and provide the ability to assess performance of a practice in real-time against outcomes, efficiency, and standards of care. Direct correlation of quality metrics to patient individualized care can be made. The capability for real-time quality improvement objectives and metrics can be supported and visualized via the dashboards provided by the dashboard generator 106.

The back office system 46 can also perform optimization of care based on individual patient symptoms and needs. The back office system 46 allows for protocols to be modified and adapted as the system learns a given patient's metrics. While current existing dosing protocols are usually based on group statistics, the rules engine 124 can implement individual protocols and algorithms 128 that can account for unique and individualized circumstances and health conditions on a patient-by-patient basis.

For the example of OAC management, the rules engine 124 can employ rule-based algorithms 128 based on a variety of patient data, such as including PT/INR values, anticoagulation dosage schedule, symptoms and responses to questions (e.g., diet, medications, and the like), and time interval between PT/INR versus potential interactions. Thus, the patient data 102 is not limited to only information obtained for a given patient from the patient unit, but can also include other data obtained for the given patient from one or more other sources. For instance, other patient data can be obtained by the back office system via an EMR interface 130, which can obtain such information from a patient's file in an EMR. Time based protocols and interactions can also be utilized by the rules engine 124 since data can be tracked individually for a given patient, which can utilize time correlations between multi-parameter measurements and questions.

The EMR interface 130 can be programmed to interface and access an EMR system (not shown), which can vary according to application requirements. For example, the EMR interface 130 can access patient and other health care records by using industry standard data protocols, such as XML or HL7. The interface 130 or other controls can be utilized to produce software standard .pdf images or other types of documents, which are searchable. A caregiver, for example, can employ back office tools to copy/paste information into other workstation/PC medical tools. As mentioned this information can include information obtained via the EMR interface 130, information from the patient data 102 as well as a combination thereof.

The patient data 102 can include a variety of data relating to the patient; such as including encounter results data 132 (e.g., test data and patient response data) obtained for a given encounter. As mentioned above, the patient data 102 can also include personal information 111, encounter instruction data 120, dosage/scheduling data 122 and other patient rules and/or logic 134. The encounter results data 132 can include information for the current encounter as well as historical data that can be access for various types of analysis or review by the caregiver. Thus, as described herein, calculations and analysis can be performed programmatically by the back office system 46 (e.g., by the rules engine 124, dashboard generator 106, report generator 108) based upon the historical and current results to help ascertain an appropriate course of treatment or recommendations. Such analysis can also be utilized to, flag certain attributes or otherwise alert a caregiver should an off-nominal condition be detected based on the established rules 126.

The personal information 111 in the patient data 102 can be stored locally, or it can be acquired from an EMR. As mentioned above, the encounter instruction data 120 can encounter questions, calls to test subroutines, as well as other patient instructions, advice or alerts that can be provided on a patient-by-patient basis in addition to patient encounter questions and other logic and rules that may be utilized by the patient unit in controlling presentation and eliciting responses from a patient.

An example of an encounter maintenance GUI 160 is depicted in FIG. 10. The encounter maintenance GUI 160 can be programmed to provide various types of information about an encounter relevant to the caregiver. The GUI can access various methods and functions to edit information and to populate the GUI with information from the database for the respective encounter. In the example of FIG. 10, the GUI 160 includes a patient information dialog element 162 that provides information for the patient (e.g., patient's name, vital statistics, such as date of birth, weight, gender, name of physician and the like). An encounter details dialog 164 can present information about the encounter such as its status (open, closed), the due date for the encounter and whether the encounter has been scheduled for the patient, such as in response to the corresponding encounter data being retrieved by the patient unit. Other information about the encounter, such as the encounter data and when information for the encounter was last updated.

The GUI 160 can also include a test results dialog 166 can be populated with test results data for the encounter provided that results have been received from the patient unit and stored in the database 30. The test results dialog 166 can also identify defined minimum and maximum values for one or more tests, as well as status information.

The GUI 160 can also include a dosage dialog 168 that can be utilized to program a next dosage for the patient. For instance, the dosage dialog 168 can be automatically populated with a suggested dosage based on a dosage function 116 and/or rules engine 124 analyzing the test results data for the encounter. The dosage dialog further can include means for editing the dosage for one or more days, such as via an edit dosage user interface element (e.g., a GUI button). The prescribed dosage for each scheduled day can be presented in the dialog 168. Alternatively, a cancel user interface element can be activated so that no changes are stored. Additionally, as mentioned herein, call log information for an encounter can be entered and linked with the encounter in a dialog box 172.

Once a caregiver has completed reviewing and/or editing the encounter information, a submit user interface element can be activated to store the updated information in the database for the corresponding encounter, such that the dosage can be retrieved by the patient unit.

Figure 4:
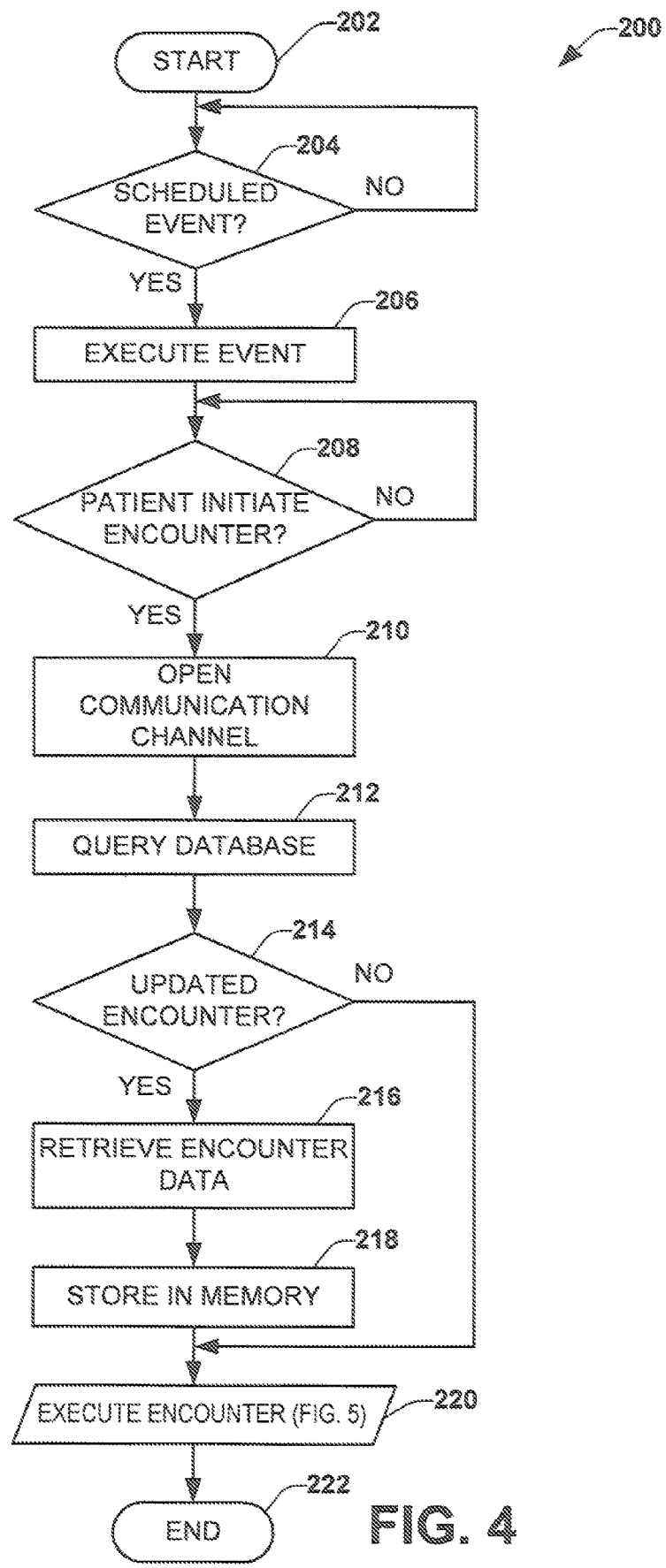
FIG. 4 is a flow diagram depicting an example method that can be implemented at a patient unit.
Figure 5:
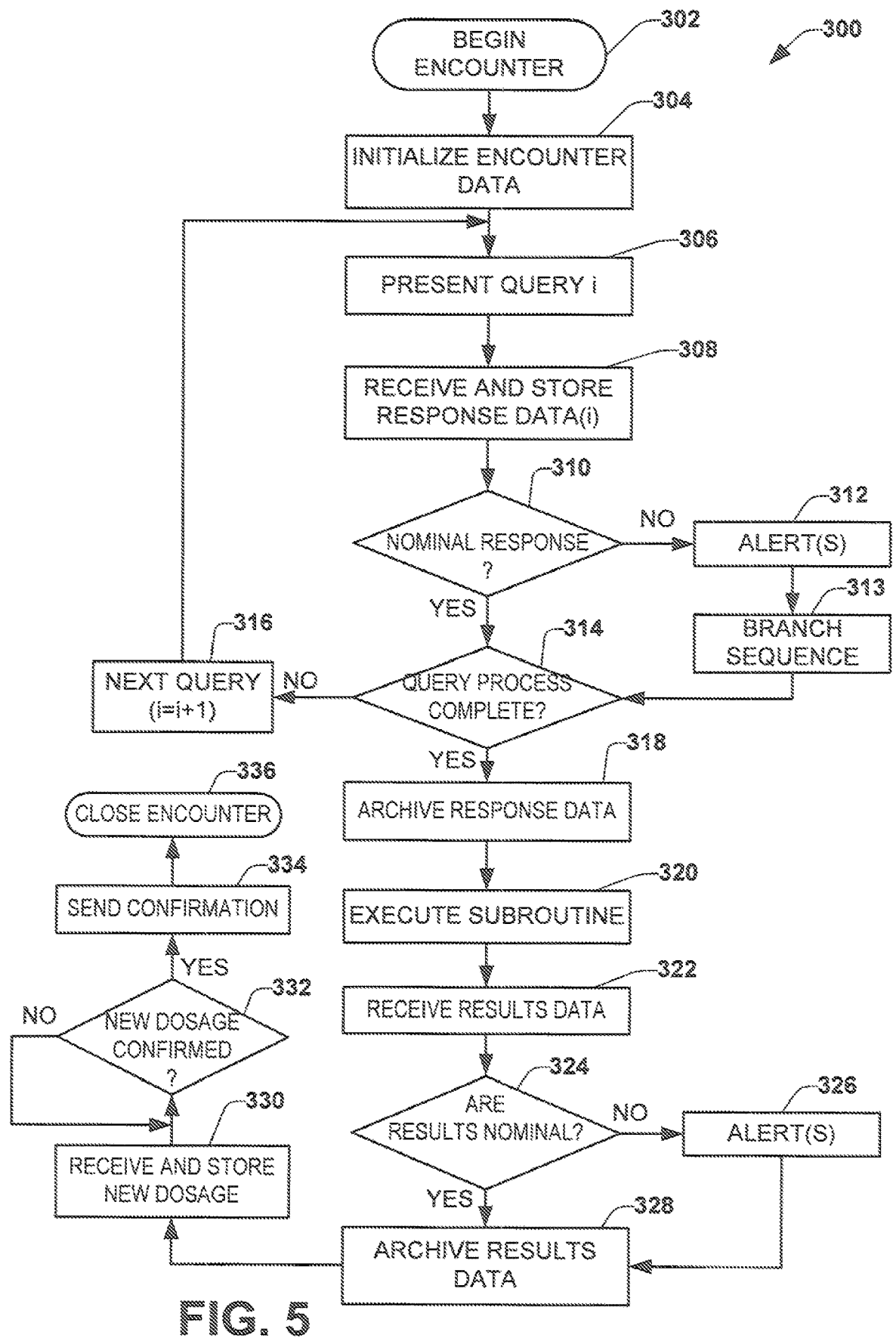
FIG. 5 is a flow diagram depicting an example of an encounter that can be implemented at a patient unit.
Figure 6:
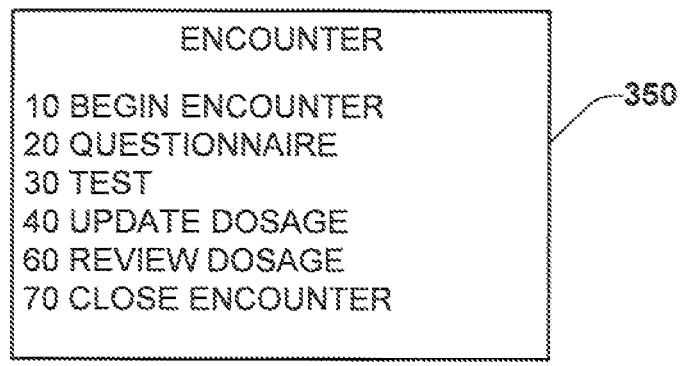
FIG. 6 depicts an example of an encounter sequence that can be implemented in a patient management system.

In view of the structural and functional features described above, certain methods will be better appreciated with reference to FIGS. 4-6. It is to be understood and appreciated that the illustrated actions, in other embodiments, may occur in different orders or concurrently with other actions. Moreover, not all features illustrated in FIGS. 4-6 may be required to implement a method. It is to be further understood that the following methodology can be implemented in hardware (e.g., one or more processors, such as in a computer or computers or special purpose computer, such as a patient unit), software (e.g., stored in a computer readable medium or as executable instructions running on one or more processors), or as a combination of hardware and software.

FIG. 4 depicts an example of a method 200 that can be implemented at a patient unit. The methodology 200 of FIG. 4 can be a patient unit 12 such as shown and described with respect to FIG. 1 or FIG. 2. Accordingly, for purposes of context and not by way of limitation, the following method 200 may be described in the context of the patient unit 12 described above.

The method 200 begins at 202, such as in conjunction with powering up the patient unit. At 202 parameters can be initialized and other housekeeping functions can be performed to prepare the unit for operation. This can include updating system resources with program code, instantiating parameters as well and loading registers to their starting values. After a device has been properly initialized the method proceeds to 204.

At 204, a determination is made as to whether a scheduled event has occurred. The scheduled event can include a scheduled patient encounter sequence, which can be stored in local memory of the patient unit (e.g., patient unit 12). If no scheduled event exists at 204 (NO), the method can remain operational and wait for a scheduled event to occur. If the determination at 204 is positive (YES) indicating that a scheduled event occurs, the method proceeds to 206 in which the scheduled event is executed. An event, for example, can include an encounter sequence or a subset of sequence of steps requiring patient interaction or other activity with the patient unit. The event can be scheduled for a day or for a specified time period, as defined by schedule data stored in local memory of the unit. Thus, while the event is being executed, the unit can provide alerts or instructions to the user via a display or other output device, based on data that is stored in the unit's memory.

At 208, a determination is made as to whether a patient initiates an encounter. As described herein, an encounter can correspond to a sequence of steps corresponding to one or more actions and/or responses provided by a patient according to the particulars of the encounter. The encounter thus can be implemented according to a predefined protocol, such as described herein. In order to initiate operation of the device, as described herein, a user may be required to enter a passcode, such as a personal identification number, via a keypad or other user interface. This can be done to ensure that the patient is individual using the device. Additionally, the patient can initiate encounter after entering the passcode by the user confirming (e.g., via an entry on the user interface of the patient unit) to begin the encounter, such as by answering affirmatively to a corresponding question or instructions presented on by the patient unit. If the patient does not initiate the encounter during the scheduled time, the unit can still permit the encounter to proceed as a late encounter, but the subsequent response data obtained for such encounter may be flagged or otherwise marked with an alert to inform the caregiver that the patient did not comply with the established protocol. Alternatively, the encounter control logic at the patient unit can instruct the user to contact the caregiver directly prior to beginning a late encounter. For instance, the user may be locked out until the caregiver authorizes the encounter to proceed via the back office system.

In response to the patient initiating the encounter at 208, the method proceeds to 210. At 210, a communication channel is opened by the patient unit. As described herein, for example, the wireless transceiver can communicate data via a desired communication protocol, such as may include cellular data (GSM), an 802.11x wireless or other protocol. At 212, the patient unit queries a remote database. The query can include a query for updated encounter instruction data, which can include executable instructions, function calls to one or more subroutines, as well as branch logic and an associated encounter a questionnaire of questions. The encounter sequence provided in the encounter instruction data defines the sequence of steps associated with the current encounter that is to begin. Since the patient unit obtains the updated instruction data in response to the user initiating the encounter (at 208), the patient will be assured that the patient unit executes the most updated encounter instructions.

At 214, a determination is made as to whether the database contains an updated encounter instruction data. If updated data exists, the method proceeds to 216 in which the unit retrieves the encounter data. It will be appreciated that the unit operates as a server programmed to access the database and retrieve information. Additionally, the patient unit operating as a server can store information in to the database. At 218, the patient unit stores the retrieved encountered data in memory. The patient unit can retrieve the encounter instruction data for the entire encounter and save the instruction data in local memory of the unit. Alternatively, the patient unit can retrieve only portions that have changed and then modify the encounter instruction data stored in its local memory.

Once the encounter instruction data has been retrieved from the remote database in response to the user initiating the encounter, the method can proceed to 220 in which the encounter is executed at the patient unit (see, e.g., FIG. 5). After the encounter has completed and is closed for the patient unit, the method 200 can end at 222. The method 200 thus can be repeated for each scheduled event such as corresponding to a set of encounters for a patient unit. The information obtained by and stored in the patient unit for a given encounter further can be stored in the remote database by the patient unit associated with the given encounter (e.g., response data and test data).

FIG. 5 depicts an example of a method 300 that can be implemented by a patient unit that performs execution of an encounter (e.g., block 220 from FIG. 4). The specifics associated with a given encounter can vary depending upon the type of condition or conditions being managed via the patient unit and the protocol defined for the patient or group of patients.

The encounter method 300 begins at 302, such as following retrieval of updated encounter data by the patient unit or if a patient has otherwise initiated an encounter. At 304, encounter data is initialized. This can include loading register values and starting the first sequence step in a given encounter, such as provided by encounter control instructions executing in a processor of the patient unit. The open encounter can also be assigned a number to uniquely identify the encounter for the patient unit and for storing in the database. The encounter method can remain open in the database until its completion as described herein. After initialization, a first query can be presented to the user, as defined by updated encounter instruction data (see, e.g., FIG. 4). At 308, the response to the query presented at 306 is received and stored as response data in memory of the patient unit. It will be appreciated that a timer function can be implemented to lock out the patient unit in the event that no response to the query (at 308) is received with in a predetermined period of time. A passcode may be required to resume the encounter, such as described herein.

At 310, a determination is made as to whether the response is a nominal response. If the response is not nominal (i.e., off-nominal), the method proceeds to 312 in which an alert can be triggered. The alert can be sent, for example, to a nurse via a data communication link, via a voice cellular communication link or a combination of data and voice communications. The type of alert can be programmed by the caregiver and can depend on the response and question. In addition to the alert (at 312), at 313, the patient unit can employ a branch sequence. The branch sequence for the encounter (at 313) can include a set of one or more predetermined questions that are relevant to the off-nominal response entered by patient. The particular protocol associated with an off-nominal response can include questions as well as performing one or more tests, which can be set by the caregiver via the back office system and programmed in the encounter instruction data. For instance, the encounter instruction data can cause the patient unit to analyze the responses and employ branch logic as part of the encounter control or encounter instruction data to cause the predetermined branch questions to be presented to the user to obtain additional information related to the preceding question and off-nominal response. The patient unit can then present the branch queries and receive responses for such queries and process the responses similar to blocks 306-310.

If the response is determined to be nominal at 310, the method proceeds from 310 to 314. At 314 a determination is made as to whether the query process (e.g., which can correspond to one or more encounter sequence step) is complete. If the query process is not complete, the method proceeds to 316 in which the next query in the sequence is accessed, such as by loading it into memory for output to the display. Thus, upon incrementing the encounter sequence, a next query can be presented at 306. Corresponding blocks 308 and 310 can be repeated for the next sequence in the encounter.

At 314, if the query process is determined to be complete (YES), the method proceeds to 318. At 318, the response data received and stored in local memory can be archived by the patient unit. The response data can include responses for the main branch of queries (blocks 306-308) as well as any responses and alerts associated with an off-nominal response (blocks 312-313). The archiving at 318 can include opening the communications channel from the patient unit to the remote database. Once the connection has been made, the response data and the corresponding questions for which they are associated can be stored in memory at the remote database (e.g., as a text file). By storing the questions and responses together or programmatically linked or joined together affords the caregiver (e.g., a nurse or other medical professional) the opportunity to review the responses provided by the patient together with exact questions that were presented to the patient.

At 320 a test subroutine is executed. The method 300 can include any number of tests or test subroutines that can be executed by the patient unit, such as may depend upon the type and purpose of the encounter. At 322, the methodology waits (e.g., in a loop) for the patient to implement the test such as via a patient measurement device. The patient unit can be in communication with the patient measurement device, such as via a direct physical connection or a wireless connection. The test subroutine can be programmed to control operation of and obtain measurement data from the measurement device as well as to control delivery of a therapy (e.g., chemical or electrical or both) to the patient. The functionality of the subroutine can be programmed according to the requirements of the protocol.

As an example, the patient measurement device as far as the test is performed can be a PT/INR test device, a blood pressure measurement device, an electronic weight scale, a breathalyzer device, an orthopedic measurement device, as well as any other device that can be utilized to measure one or more conditions or characteristics of the patient. Additionally or alternatively, the device can also be utilized to control delivery of a therapy to the patient. The patient unit can present a query to the patient to confirm that the therapy has been delivered or that the test has been completed in compliance with the established protocol. Those skilled in the understand that the methodology and system shown and described herein are not limited by type of device but can have global applicability to various types of devices that can be acted upon and controlled for monitoring or measuring various conditions of the patient or delivering drugs and dosage to the patient.

At 322, the results of the test subroutine are received. As mentioned above, the results can be received by the patient unit directly via communication with the device or, in some cases, the results can be entered by the patient into the patient unit. At 324 a determination is made as to whether the results are nominal. If the results are not nominal (e.g., not within expected operating parameter), the method proceeds to 326 in which a corresponding alert can be triggered. The alert at 326 can be similar to the alert at 312 in that it can be sent to one or more predefined destinations in response to detecting the off-nominal test results. Additionally, or alternatively, the alert can be stored with the results data in the patient unit.

If the results are nominal, the method proceeds to 328 in which the results data for the patient encounter is archived. Similar to the archival at 318, the archiving of the results data at 328 can involve opening a data communication channel via a wireless link (e.g., cellular, GSM or Wi-Fi) to the remote database and the patient unit operating as a server for storing the test data for the currently open encounter in the database (e.g., as a text file). In this way, patient data records in the database can include set of different encounters that can occur at different times each of which can include response data and test data. While the data is being archived, the patient unit can display a message to indicate that data is being sent and that the results will be reviewed by a certain time and date (e.g., a message like: "Sending data . . . your results will be reviewed at noon today.").

From 328, the method proceeds to 330 in which the patient unit can receive and store a new dosage and schedule. The new dosage can include a dosage for chemical therapy or drug therapy, physical therapy, or any number of one or more conditions or behaviors that can be managed for the patient. Alternatively or additionally, the dosage received at 330 can be utilized to control a patient device (e.g., the device 14 or 14' of FIG. 2) to deliver and/or control delivery of a treatment or therapy to the patient according to the defined schedule.

As one example, for OAC management, the dosage received at 330 can correspond to an amount of warfarin or other anticoagulant that a given patient is to consume at a prescribed interval over a predetermined time period. Thus, the dosage can provide sufficient details for the patient until a next encounter is scheduled to occur. The dosage for the patient can be presented on the display of the patient unit, such as listing the amount and time that each dosage is to be taken by the patient. The data received at 330 can also include schedule data that defines when the next encounter for the patient is scheduled to occur. Thus, it will be appreciated that between blocks 326 and 328, it is incumbent upon the caregiver to review the results and submit a new dosage and schedule. As disclosed herein, this can be caregiver controlled and then automatically generated, semi-automatically generated (e.g., a suggested dosage and schedule confirmed by the caregiver) or fully manually generated by the caregiver.

At 332, the patient unit determines whether the patient has explicitly confirmed the new dosage and scheduled. If the patient does not confirm the new dosage, the method can loop for a predetermined period of time and if the patient does not confirm in such period of time, an alert can be provided to a medical professional or other specified individual or service. The encounter can remain in the open state indefinitely until it is either closed by the caregiver or the patient confirms the dosage at 332. If the patient confirms the new dosage, thereby complying with the dosage, the patient unit can send a confirming message back to the database, which can inform the caregiver of the patient's compliance with the protocol. Once the confirmation is stored in the database by the patient unit, the encounter can be changed from open to closed at 336, such as by the patient unit changing a the encounter status field from open to closed. This status change for the encounter from open to closed, will also remove the encounter from the listing of unclosed encounters, which can be viewed and managed by the caregiver.

Figure 7:
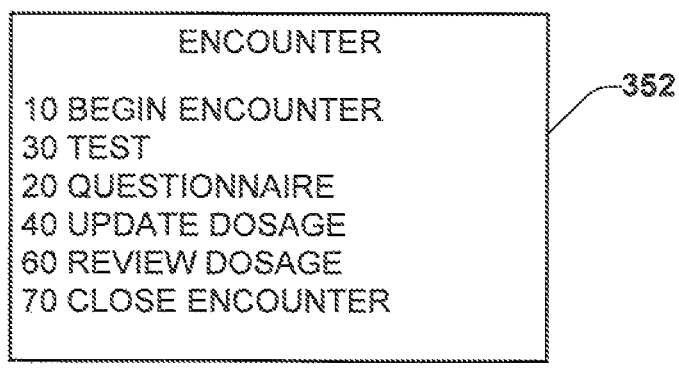
FIG. 7 depicts an example of a first modified encounter sequence that can be implemented in a patient management system.
Figure 8:
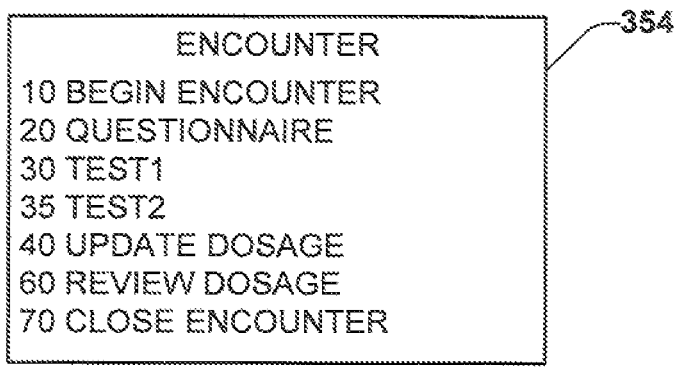
FIG. 8 depicts an example of a second modified encounter sequence that can be implemented in a patient management system.

FIGS. 6, 7 and 8 depict examples of different encounters that can be provided as part of encounter instruction data, which can be managed and updated for a given patient by a caregiver via a caregiver user interface accessing an encounter maintenance function running in the back office system. Each encounter includes a series of steps. An aggregate set of steps can be stored in the database from which a caregiver can select which of the available steps to include and the order of steps for each given encounter.

In FIG. 6, an encounter 350 includes six steps indicated at 10, 20, 30, 40, 60 and 70, as demonstrated in FIG. 6. Each of these steps can be implemented as part of an encounter for a given patient and can involve a variety of actions that require interactions (responses and/or other activity) by the patient or by the caregiver or both by the patient and caregiver. It is to be understood that the practitioner can modify an encounter by changing the order of steps in a sequence. That is, the numbers do not specify the order of steps in the sequence but can be provided in the database in a manner that can facilitate accessing and editing and updating an encounter sequence for a patient or group of patients.

For example, the encounter 352 in FIG. 7 demonstrates that the encounter has been modified in which the test sequence step (30) has been moved in the sequence before the questionnaire of sequence step (20). In FIG. 8, the encounter 356 has been modified relative to the encounter sequence 350 of FIG. 6 by adding a new step, namely, a second test identified as sequence number 35 for execution by the patient unit following the test at sequence step (30).

As will be appreciated by those skilled in the art, portions of the invention may be embodied as a method, data processing system, or computer program product. Accordingly, these portions of the invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention are described herein with reference to flowchart illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to, produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Although the innovation has been shown and described with respect to certain illustrated aspects, it will be appreciated that equivalent alterations and modifications will occur to others skilled in the art upon the reading and understanding of this specification and the annexed drawings. In particular regard to the various functions performed by the above described components (assemblies, devices, circuits, systems, etc.), the terms (including a reference to a "means") used to describe such components are intended to correspond, unless otherwise indicated, to any component which performs the specified function of the described component (e.g., that is functionally equivalent), even though not structurally equivalent to the disclosed structure, which performs the function in the herein illustrated exemplary aspects of the innovation. Furthermore, to the extent that the terms "includes", "including", "has", "having", and variants thereof are used in either the detailed description or the claims, these terms are intended to be inclusive in a manner similar to the term "comprising."

What is claimed is:

1. A patient monitoring system comprising:
a patient unit configured as a server in a network to read and write data in a remote database, the patient unit comprising:
a device interface configured to provide for data communication with a measurement device, the patient unit being programmed to selectively retrieve results data indicative of at least one patient condition from the measurement device;
a communication module configured to provide two-way communication via the network with the remote database, the server being configured to employ the communication module to retrieve encounter instruction data for the patient unit from the remote database for a given patient encounter, the encounter instruction data comprising a plurality of main sequence steps that include at least one set of pre-determined queries, at least one of the plurality of main sequence steps being programmed to trigger a conditional branch of sequence steps in response to detecting an off-nominal condition at the at least one of the plurality of sequence steps, the conditional branch of sequence steps being programmed to obtain additional information about the off-nominal condition and to return to complete the plurality of main sequence steps, the patient unit disabling the measurement device via the device interface until the plurality of main sequence steps and the conditional branch of sequence steps, as provided by the encounter instruction data, are completed to prevent a premature measurement of the at least one patient condition and ensure compliance with a patient specific protocol, the patient unit providing a command via the device interface to enable the measurement device to measure the at least one patient condition after the plurality of main sequence steps and the conditional branch of sequence steps are completed, the server being configured to employ the communication module to send response data to the remote database for the given patient encounter, the response data comprising stored user responses, including the additional information about the off-nominal condition, and the results data; and a user interface programmed to present at least one of the predetermined queries to a user and to receive user responses to the each of the predetermined queries for the given patient encounter, the user responses for each of the predetermined queries being stored in memory of the patient unit as the response data for the given encounter; and a back office system programmed to access the remote database and to retrieve the response data from the remote database for at least one patient unit, the back office system further being programmed to at least one of add or modify the encounter instruction data in response to retrieved response data for the given encounter, the encounter instruction data being stored in the remote database for a next patient encounter at the patient unit.

2. The system of claim 1, wherein the at least one patient condition comprises an indication of blood coagulation for the patient.

3. The system of claim 1, wherein the patient unit further comprises controls for selectively enabling the measurement device to operate according to a predefined sequence step of the given patient encounter and disabling operation of the measurement device at steps prior to the predefined sequence step based on the encounter instruction data.

4. The system of claim 1, wherein the patient unit further comprises controls for selectively enabling the measurement device to operate after at least a predetermined sequence step of the given patient encounter has been completed.

5. The system of claim 4, wherein the patient unit further comprises controls configured to instruct the measurement device to at least one of control delivery of a therapy or dosage to the patient according to execution of a predefined sequence step of the given patient encounter based on the encounter instruction data defined for a given patient protocol.

6. The system of claim 1, wherein the at least one patient condition is analyzed based on the response data, including the results data, to ascertain compliance with a therapy or dosage for the given patient, wherein the at least one patient condition is analyzed by at least one of the patient unit and the back office system to ascertain the compliance.

7. The system of claim 1, wherein the at least one patient condition comprises an information about an orthopedic condition for the patient.

8. The system of claim 1, wherein the patient unit is programmed to store the response data separately from the results data.

9. The system of claim 1, wherein the patient unit is programmed to employ the communication module to retrieve updated instruction data from the remote database in response the user initiating a new encounter, the updated instruction data including a sequence of steps to be executed for the new encounter, at least some of the sequence of steps to be executed for the new encounter being determined based on a set of historical patient data for the patient.

10. The system of claim 1, wherein the patient unit comprises an encounter schedule that indicates when the given encounter is scheduled to begin, the encounter schedule being stored in the memory of the patient unit in response to schedule data retrieved from the remote database as part of a preceding encounter that was substantially completed prior to the given encounter.

11. The system of claim 1, wherein the patient unit comprises a test subroutine for controlling acquisition of the results data from the measurement device, the patient unit calling the test subroutine in response to executing a predefined sequence step of the given encounter.

12. The system of claim 1, wherein the given encounter comprises a sequence of predefined steps according to an established patient procedure protocol, at least a substantial portion of the sequence of predefined steps requesting a confirmation response to be entered into the patient unit via the user interface, wherein the response data for the given encounter further comprises an indication of the confirmation response to indicate the user's compliance with the established patient procedure protocol if the confirmation response is compliant or to indicate the user's non-compliance with the established patient procedure protocol if the confirmation response is negative or non-compliant.

13. The system of claim 12, wherein the sequence of predefined steps comprises an update dosage sequence step, the patient unit retrieving an updated dosage for the given encounter from the remote database during execution of the update dosage sequence step, the update dosage sequence step employing instructions requesting that the user enter a dosage confirmation response via the user interface during the given encounter at the patient unit to indicate that the user has received the updated dosage for a next treatment interval.

14. The system of claim 1, wherein the patient unit further comprising an alarm function that generates an alert in response to the off-nominal condition or non-compliance being detected in at least one of the response data and the results data.

15. The system of claim 14, wherein the patient unit is programmed to generate a real time alert that is provided to a predefined recipient in response to detecting the off-nominal condition.

16. The system of claim 1, wherein the back office system comprises a dosage function that is programmed to determine a suggested dosage schedule for a next treatment interval in response to encounter response data and results data from the patient unit for at least the given encounter and historical patient data that includes response data from at least one encounter at the patient unit prior to the given encounter.

17. The system of claim 16, wherein the back office system comprises a caregiver user interface that is programmed to at least one of accept and modify the suggested dosage schedule based on a user input and generate corresponding dosage data that is stored in the remote database for retrieval by the patient unit as part of the given encounter.

18. A patient monitoring system comprising:
a patient unit configured as a server in a network to read and write data in a remote database, the patient unit comprising:
a device interface configured to provide for data communication with a measurement device, the patient unit being programmed to selectively retrieve results data indicative of at least one patient condition that is measured by the measurement device;
a communication module configured to provide two-way communication with the remote database via the network, the server configured to employ the communication module to retrieve encounter instruction data for the patient unit from the remote database for a given patient encounter that includes a plurality of predefined sequence steps that involve at least one set of predetermined queries to be presented to the user for the given patient encounter, at least one of the plurality of predefined sequence steps being programmed to trigger a conditional branch of sequence steps in response to detecting an off-nominal condition at the at least one of the plurality of predefined sequence steps, the conditional branch of sequence steps being programmed to obtain additional information about the off-nominal condition and to return to complete the plurality of predefined sequence steps, the patient unit disabling the measurement device via the device interface until the plurality of predefined sequence steps and the conditional branch of sequence steps, as provided by the encounter instruction data, are completed to prevent a premature measurement of the at least one patient condition and ensure compliance with a patient specific protocol, the patient unit providing a command via the device interface to enable the measurement device to measure the at least one patient condition after the plurality of predefined sequence steps and the conditional branch of sequence steps are completed, the server also being configured to employ the communication module to send response data to the remote database for the given patient encounter, the response data comprising at least one of stored user responses and the results data;

a user interface programmed to present at least one of the predetermined queries to a user and to receive user responses to the each of the predetermined queries for the given patient encounter based on the encounter instruction data, the user responses for each of the predetermined queries being stored in memory of the patient unit as the response data for the given encounter; and a back office system programmed to access the remote database and to retrieve the response data from the remote database for at least one patient unit, the back office system further being programmed to at least one of add or modify the encounter instruction data that is stored in the remote database for a next patient encounter at the patient unit, wherein the back office system comprises a rules engine that includes predetermined rules programmed according to a predetermined patient procedure protocol, the back office system employing the rules to generate the encounter instruction data that is retrieved by the patient unit during the given encounter to modify at least one of the plurality of predefined sequence steps;

wherein the sequence of predefined steps comprises an update dosage sequence step, the patient unit retrieving an updated dosage instruction for the given encounter from the remote database during execution of the update dosage sequence step of the given encounter, a dosage query being presented as part of the update dosage sequence step, based on the instruction data, requesting that the user enter a dosage confirmation response via the user interface of the patient unit, the dosage confirmation response being stored as response data in the remote database to indicate that the user has received the updated dosage instruction for a next treatment interval.

19. The system of claim 18, wherein the predetermined rules are programmable via the back office system on a patient-by-patient basis to provide individualized care for at least two different patients.

20. The system of claim 18, wherein the rules engine is programmed to automatically generate at least one of a dosage schedule and the encounter instruction data.

21. A method for remote patient management, comprising:

initiating a given encounter at a patient unit in response to a user input provided at the patient unit;

opening a two-way wireless communication channel between the patient unit and a remote database, such that the patient unit operates as a server to retrieve encounter instruction data for the given encounter and an updated dosage from the remote database from the remote database, the encounter instruction data defining a sequence of steps including at least one set of predetermined queries to be executed at the patient unit for the given encounter according to a predetermined patient procedure protocol, wherein the sequence of steps of the given encounter further comprises an update dosage sequence step;

executing the update dosage sequence step of the given encounter to store the updated dosage in memory of the patient unit;

requesting that a user enter a confirmation response at the patient unit to indicate that the user has received the updated dosage for a next treatment interval;

executing each of the sequence of steps at the patient unit, at least some of the sequence of steps requesting responses from the user to confirm compliance with the respective step and at least one of the sequence of steps corresponding to test subroutine;

executing the test subroutine at the patient unit to receive results data indicative of a patient condition;

sending response data for the given encounter from the patient unit to the remote database via a communication channel;

retrieving by the patient unit updated encounter instruction data from the remote database for a next encounter at the patient unit, the updated encounter instruction data being generated based on the response data, which is sent to and stored in the remote database for the given encounter, and based on historical patient data, corresponding to response data from at least one previous encounter at the patient unit, to provide a sequence of steps to be executed at the patient unit for the next encounter at the patient unit;

detecting an off-nominal condition in at least one of the sequence of steps;

triggering a conditional branch of sequence steps in response to the detection of the off-nominal response;

obtaining additional information about the off-nominal condition; and disabling a measurement device via a device interface of the patient unit until the sequence of steps, the at least one set of predetermined queries, and the conditional branch of sequence steps, as provided by the encounter instruction data, are completed to prevent a premature measurement of the patient condition and ensure compliance with a patient predetermined patient procedure protocol, the patient unit providing a command via the device interface to enable the measurement device to measure the patient condition.

22. The method of claim 21, further comprising receiving the results data at the patient unit via at least one of a communication link between the patient unit and a separate patient measurement device that is configured to measure the patient condition.

23. The method of claim 21, further comprising receiving the results data at the patient unit via a user input entered into to the patient unit via a user interface of the patient unit.

24. The method of claim 21, wherein in response to evaluating at least one of the response data and results data for the given encounter at a back office system, the method further comprises determining at the back office system a suggested dosage schedule for the patient according to the predetermined patient procedure protocol, the suggested dosage scheduled being stored as part of the updated encounter instruction data in the remote database for retrieval by the patient unit.

25. The method of claim 24, further comprising providing a caregiver user interface that is programmed to at least one of accept and modify the suggested dosage schedule based on a user input from a caregiver;
storing corresponding dosage data in the remote database; and
retrieving the dosage data from the remote database by the patient unit as part of the given encounter.

26. A patient monitoring system comprising:
a patient unit configured as a server in a network, the patient unit comprising:
a device interface configured to provide for data communication with a measurement device;
a communication device module configured to provide two-way communication via the network with a remote database, the communication module being configured to retrieve encounter instruction data for the patient unit from the remote database for a given patient encounter, the encounter instruction data comprising a plurality of main sequence steps that include at least one set of predetermined queries;
a processor to access memory and to execute instructions stored in the memory;
the memory being configured to store the instructions and the encounter instruction data, the instructions being programmed to:
selectively retrieve results data indicative of at least one patient condition from the measurement device via the device interface;
trigger conditional branch sequence steps in response to detecting an off-nominal condition at the at least one of the plurality of main sequence steps, the conditional branch of sequence steps being programmed to obtain additional information about the off-nominal condition and to return to complete the plurality of main sequence steps of the given patient encounter, the patient unit disabling the measurement device via the device interface until the plurality of main sequence steps and the conditional branch of sequence steps, as provided by the encounter instruction data, are completed to prevent a premature measurement of the at least one patient condition and ensure compliance with a patient specific protocol, the patient unit providing a command via the device interface after the plurality of main sequence steps and the conditional branch of sequence steps are completed to enable the measurement device to measure the at least one patient condition;
employ the communication module to send response data to the remote database for the given patient encounter, the response data comprising stored user responses, including the additional information about the off-nominal condition, and the results data; and
present via a user interface at least one of the predetermined queries to a user and to receive user responses to the each of the predetermined queries for the given patient encounter, the user responses for each of the predetermined queries being stored in memory of the patient unit as the response data for the given encounter;
wherein the plurality of main sequence steps further includes an update dosage sequence step, the patient unit retrieving an updated dosage for the given encounter from the remote database during execution of the update dosage sequence step, the update dosage sequence step employing instructions to request that the user enter a dosage confirmation response via the user interface at the patient unit to indicate that the user has received the updated dosage for a next treatment interval.

27. The system of claim 26, wherein the patient unit is programmed to generate a real time alert that is provided to a predefined recipient in response to detecting the off-nominal condition and to receive a confirmation in response to a user input entered via the user interface to acknowledge receipt of the alert by the patient.

28. The system of claim 26, wherein the detected off-nominal condition is determined based on a response to a given one of the predetermined queries that is entered at the patient unit via the user interface.

29. The system of claim 26, wherein the updated dosage is determined based on user responses during the given encounter and based on historical trends derived from the response data from at least one previous encounter at the patient unit.

* * * * *